(12) United States Patent
Kulagowski et al.

(10) Patent No.: US 6,555,552 B2
(45) Date of Patent: Apr. 29, 2003

(54) AZABICYCLIC AMINE DERIVATIVES AND THEIR USE AS THERAPEUTIC AGENTS

(75) Inventors: Janusz Jozef Kulagowski, Sawbridgeworth (GB); Piotr Antoni Raubo, Bishops Stortford (GB); Christopher George Thomson, Bishops Stortford (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 0 days.

(21) Appl. No.: 10/113,965

(22) Filed: Apr. 1, 2002

(65) Prior Publication Data
US 2002/0147212 A1 Oct. 10, 2002

(30) Foreign Application Priority Data
Apr. 10, 2001 (GB) .............................................. 0109871

(51) Int. Cl.[7] .......................... A61K 31/46; C07D 45/02
(52) U.S. Cl. ........................ 514/304; 546/133; 546/223; 546/124; 546/304; 514/305; 514/329
(58) Field of Search ................................ 514/305, 329, 514/304; 546/133, 223

(56) References Cited

U.S. PATENT DOCUMENTS

2002/0049211 A1 * 4/2002 Beth ........................... 514/250

FOREIGN PATENT DOCUMENTS

WO WO 2001077100 * 10/2001

* cited by examiner

Primary Examiner—Joseph K. McKane
Assistant Examiner—Rei-Tsang Shiao

(74) Attorney, Agent, or Firm—J. Eric Thies; Melvin Winokur; Baerbel R. Brown

(57) ABSTRACT

The present invention relates compounds of the formula (I):

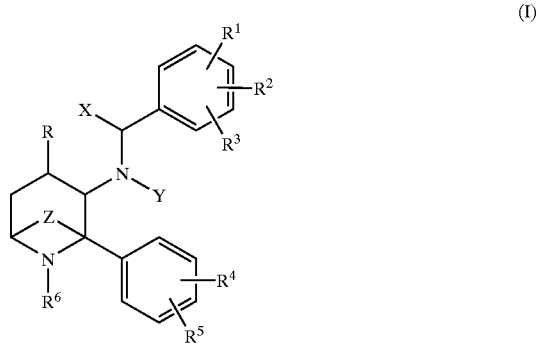

(I)

wherein
  X represents hydrogen or a $C_{1-4}$alkyl group optionally substituted by a hydroxy group;
  Y represents hydrogen, $C_{1-6}$alkyl or $C_{3-7}$cycloalkyl;
  Z is —$CR^9R^{10}CH_2$— or —$CH_2CR^9R^{10}$—;
  R represents hydrogen, fluorine, hydroxy, $C_{1-6}$alkyl or $C_{1-6}$alkoxy;
  and $R^1$, $R^2$, $R^3$, $R^4$, $R^5$ and $R^6$ are as defined herein.

The compounds are of particular use in the treatment of depression, anxiety, pain, inflammation, migraine, emesis or postherpetic neuralgia.

19 Claims, No Drawings

AZABICYCLIC AMINE DERIVATIVES AND THEIR USE AS THERAPEUTIC AGENTS

CROSS REFERENCE TO RELATED APPLICATIONS

This application claims priority under 35 U.S.C. §119 from GB Application No. 0108971.3, filed Apr. 10, 2001.

The present invention provides compounds of the formula (I):

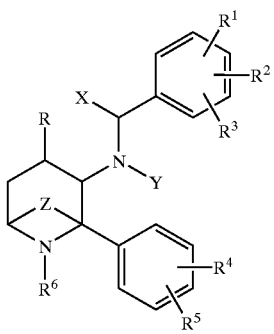

wherein

X represents hydrogen or a $C_{1-4}$alkyl group optionally substituted by a hydroxy group;

Y represents hydrogen, $C_{1-6}$alkyl or $C_{3-7}$cycloalkyl;

Z is —$CR^9R^{10}CH_2$— or —$CH_2CR^9R^{10}$—;

R represents hydrogen, fluorine, hydroxy, C16alkyl or $C_{1-6}$alkoxy;

$R^1$ represents hydrogen, hydroxy, $C_{1-6}$alkyl, $C_{2-6}$alkenyl, $C_{3-7}$cycloalkyl, $C_{3-7}$cycloalkyl$C_{1-4}$alkyl, $C_{1-6}$alkoxy, fluoro$C_{1-6}$alkoxy, hydroxy$C_{1-6}$alkyl, $C_{1-6}$alkoxy$C_{1-4}$alkyl, $C_{1-6}$alkoxy$C_{1-4}$alkoxy, fluoro$C_{1-6}$alkoxy$C_{1-4}$alkyl, $C_{2-6}$alkenyloxy, $C_{3-7}$cycloalkoxy, $C_{3-7}$cycloalkyl$C_{1-4}$alkoxy, phenoxy, benzyloxy, cyano, halogen, $NR^aR^b$, $SR^a$, $SOR^a$, $SO_2R^a$, $OSO_2R^a$, $NR^aCOR^{12}$, $COR^a$, $CO_2R^a$ or $CONR^aR^b$ where $R^a$ and $R^b$ each independently represent hydrogen, $C_{1-4}$alkyl or fluoro$C_{1-4}$alkyl;

$R^2$ represents hydrogen, halogen, $C_{1-6}$alkyl or $C_{1-6}$alkoxy;

or when R2 is adjacent to $R^1$, they may be joined together such that there is formed a 5- or 6-membered saturated or unsaturated ring containing one or two atoms selected from nitrogen, oxygen, sulphur, NH or $NR^c$, which ring is optionally substituted by one, two or three groups selected from hydroxy, $C_{1-4}$alkyl, $C_{1-3}$alkoxy$C_{1-3}$alkyl, fluoro$C_{1-4}$alkyl, phenyl, =O or =S, where $R^c$ represents $C_{1-4}$alkyl, hydroxy$C_{1-4}$alkyl, $C_{1-4}$alkoxy$C_{1-4}$alkyl, fluoro$C_{1-4}$alkyl, phenyl or benzyl.

$R^3$ represents hydrogen, halogen, $C_{1-6}$alkyl, fluoro$C_{1-6}$alkyl, $C_{1-6}$alkoxy, fluoro$C_{1-6}$alkoxy, $C_{3-7}$cycloalkyl, $C_{3-7}$cycloalkyl$C_{1-4}$alkyl, cyano, $SR^a$, $SOR^a$, $SO_2R^a$, $NR^aR^b$, $NR^aCOR12$, $COR^a$, $CO_2R^a$, $CONR^aR^b$ or $C_{1-4}$alkyl substituted by cyano, $CO_2R^a$ or $CONR^aR^b$ where $R^a$ and $R^b$ are as previously defined;

or $R^3$ represents a 5- or 6-membered aromatic heterocyclic group containing 1, 2, 3 or 4 heteroatoms, selected from nitrogen, oxygen and sulphur, which group is optionally substituted by one or two groups selected from $C_{1-6}$alkyl, $C_{1-6}$alkoxy, $C_{3-7}$cycloalkyl, $C_{3-7}$cycloalkyl$C_{1-4}$alkyl, trifluoromethyl, $OCF_3$, $NO_2$, CN, $SR^a$, $SOR^a$, $SO_2R^a$, $COR^a$, $CO_2R^a$, phenyl, —$(CH_2)_rNR^aR^b$, $(CH_2)_rNR^aCOR_b$, $(CH_2)_rCONR^aR^b$, or $CH_2C(O)R^a$, where $R^a$ and $R^b$ are as previously defined and r is zero, 1 or 2;

$R^4$ represents hydrogen, halogen, $C_{1-6}$alkyl, $C_{1-6}$alkoxy, $CF_3$, $OCF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, where $R^a$ and $R^b$ are as previously defined;

$R^5$ represents hydrogen, halogen, $C_{1-6}$alkyl, $CF_3$ or $C_{1-6}$alkoxy substituted by $C_{1-4}$alkoxy;

$R^6$ represents hydrogen, hydroxy, $COR^a$, $CO_2R^a$, $COCONR^aR^b$, $COCO_2R^a$, $C_{1-6}$alkyl optionally substituted by a group selected from ($CO_2R^a$, $CONR^aR^b$, hydroxy, CN, $COR^a$, $NR^aR^b$, $C(NOH)NR^aR^b$, CONHphenyl($C_{1-4}$alkyl), $COCO_2R^a$, $CONHNR^aR^b$, $C(S)NR^aR^b$, $CONR^aC_{1-6}$alkyl$R^{14}$, $CONR^{11}C_{2-6}$alkenyl, $CONR^{11}C_{2-6}$alkynyl, $COCONR^aR^b$, $CONR^aC(NR^b)NR^aR^b$, $CONR^a$heteroaryl, and phenyl optionally substituted by one, two or three substituents selected from $C_{1-6}$alkyl, $C_{1-4}$alkoxy, halogen and trifluoromethyl);

or $R^6$ represents a group of the formula —$CH_2C{\equiv}CCH_2NR^7R^8$ where $R^7$ and $R^8$ are as defined below;

or $R^6$ represents $C_{1-6}$alkyl, optionally substituted by oxo, substituted by a 5-membered or 6-membered heterocyclic ring containing 1, 2 or 3 nitrogen atoms optionally substituted by =O or =S and optionally substituted by a group of the formula —W—$NR^7R^8$ where W is $C_{1-6}$alkylene or $C_{3-6}$cycloalkyl;

$R^7$ represents hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy or hydroxyl;

$R^8$ represents hydrogen or $C_{1-4}$alkyl, $C_{1-4}$alkoxy, $C_{3-7}$cycloalkyl, $C_{3-7}$cycloalkyl$C_{1-4}$alkyl, or $C_{2-4}$alkyl substituted by a group selected from $C_{1-4}$alkoxy, hydroxyl, $CO_2R^a$, $NR^aR^b$, aryl, aryloxy, heteroaryl or a 4, 5 or 6 membered heteroaliphatic ring containing one or two heteroatoms selected from N, O and S;

or $R^7$, $R^8$ and the nitrogen atom to which they are attached form a heteroaliphatic ring of 4 to 7 ring atoms, optionally substituted by one or two groups selected from hydroxy, phenyl, benzyl or $C_{1-4}$alkoxy optionally substituted by a $C_{1-4}$alkoxy or hydroxyl group, and optionally containing a double bond, which ring may optionally contain an oxygen or sulphur ring atom, a group S(O) or $S(O)_2$ or a second nitrogen atom which will be part of a NH or NRC moiety where $R^c$ is as previously defined;

or $R^7$, $R^8$ and the nitrogen atom to which they are attached form a non-aromatic azabicyclic ring system of 6 to 12 ring atoms;

or W, $R^7$ and the nitrogen atom to which they are attached form a heteroaliphatic ring to 4 to 7 ring atoms which may optionally contain an oxygen ring atom;

$R^9$ represents hydrogen, hydroxy, oxo, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, fluoro$C_{1-6}$alkyl, $C_{1-6}$alkoxy, fluoro$C_{1-6}$alkoxy, hydroxy$C_{1-6}$alkyl, $C_{1-6}$alkoxy$C_{1-4}$alkyl, $C_{1-6}$alkoxy$C_{1-4}$alkoxy, fluoro$C_{1-6}$alkoxy$C_{1-4}$alkyl, $C_{2-6}$alkenyloxy, $C_{2-6}$alkynyloxy, $C_{3-7}$cycloalkoxy, $C_{3-7}$cycloalkyl$C_{1-4}$alkoxy, aryl, aryl($CH_2$), aryloxy, aryl($CH_2$)oxy, cyano, halogen, $NR^7R^8$, $CH_2NR^7R^8$, $SR^{12}$, $SOR^{12}$, $SO_2R12$, $OSO_2R^{12}$, $NR^aCOR^{12}$, $CH(OH)R^{12}$, COR$^{12}$, CO$_2$R$^{12}$, CONR$^7$R$^8$ CH$_2$OR$^{13}$, heteroaryl or heteroarylC$_{1-4}$alkyl, wherein R$^a$ is as previously defined;

R$^{10}$ represents hydrogen, halogen or hydroxy;

R$^{11}$ represents hydrogen or C$_{1-6}$alkyl;

R$^{12}$ represents hydrogen, C$_{1-6}$alkyl, C$_{1-6}$alkoxy, fluoroC$_{1-6}$alkyl or phenyl optionally substituted by one, two or three substituents selected from C$_{1-6}$alkyl, C$_{1-6}$alkoxy, halogen or trifluoromethyl;

R$^{13}$ represents C$_{1-4}$alkyl substituted by a group selected from hydroxy, COR$^a$, CO$_2$R$^a$, CONR$^a$R$^b$ and heteroaryl, where R$^a$ is as previously defined;

R$^{14}$ represents OR$^a$, CONR$^a$R$^b$ or heteroaryl;

and pharmaceutically acceptable salts or N-oxides thereof.

A preferred class of compound of formula (I) is that wherein X is hydrogen, methyl or hydroxymethyl, in particular, hydrogen.

Another preferred class of compound of formula (I) is that wherein Y is hydrogen or C$_{1-4}$alkyl, in particular, hydrogen or methyl, especially hydrogen.

A further preferred class of compounds of formula (I) is that wherein R represents hydrogen or fluorine.

A preferred class of compound of formula (I) is that wherein R$^1$ is a C$_{1-6}$alkoxy, fluoroC$_{1-6}$alkoxy or C$_{3-7}$cycloalkoxy group, or R$^1$ together with the group R$^2$ forms a 5-membered saturated ring containing one oxygen atom, which ring is optionally substituted by a methyl group.

A particularly preferred class of compound of formula (I) is that wherein R$^1$ is methoxy, trifluoromethoxy, 2,2,2-trifluoroethoxy, 2,2-difluoroethoxy, 2-fluoroethoxy, cyclopropoxy or R$^1$ together with the group R$^2$ represents —OCH(CH$_3$)CH$_2$— or —N(CH$_3$)C(O)C(CH$_3$)$_2$— to complete a 5-membered saturated ring, or —CH(OH)CH$_2$OC(CH$_3$)(CF$_3$)—, —CH$_2$CH$_2$C(O)N(CH$_3$)— or —CH(OH)CH$_2$C(O)N(CH$_3$)— to complete a 6-membered saturated ring. Most especially, R$^1$ is methoxy or cyclopropoxy.

Another preferred class of compound of formula (I) is that wherein R$^2$ is a hydrogen, fluorine or chlorine atom, especially a hydrogen atom.

A further preferred class of compound of formula (I) is that wherein R$^3$ is a hydrogen or halogen atom or a fluoroC$_{1-6}$alkoxy group, especially fluorine, trifluoromethoxy or 2,2,2-trifluoroethoxy, or a 5-membered aromatic heterocyclic group as previously defined. Most especially, R3 is trifluoromethoxy or 5-(trifluoromethyl)tetrazol-1-yl.

A particularly preferred class of compound of formula (I) is that wherein R$^1$ is attached at the 2-position of the phenyl ring and R$^3$ is attached at the 5-position of the phenyl ring.

A further preferred class of compound of formula (I) is that wherein R$^4$ is a hydrogen atom or a fluorine atom.

Another preferred class of compound of formula (I) is that in which R$^5$ is a hydrogen atom.

A further preferred class of compound of formula (I) is that wherein R$^6$ is a hydrogen atom or a C$_{1-6}$alkyl group. Most especially, R$^6$ is hydrogen or methyl.

Also preferred is the class of compound of formula (I) in which R$^6$ is a C$_{1-6}$alkyl group, in particular CH$_2$, CH(CH$_3$) and CH$_2$CH$_2$ and especially CH$_2$, substituted by a 5-membered heterocyclic ring containing 2 or 3 nitrogen atoms as previously defined.

In particular, the 5-membered ring is a heterocyclic ring selected from 1,3-imidazol-4-yl, 1,2,4-triazol-3-yl, 1,2,3-triazol-4-yl, 2-oxo-1,3-imidazol-4-yl, and 3-oxo-1,2,4-triazol-5-yl, any of which rings being optionally substituted by the group —W—NR$^7$R$^8$.

Particularly preferred heterocyclic rings are selected from:

Another preferred class of compound of formula (I) is that wherein R$^9$ represents hydrogen, hydroxy, oxo, C$_{1-6}$alkoxy, C$_{1-6}$alkoxyC$_{1-4}$alkyl, hydroxyC$_{1-4}$alkyl, cyano, NR$^7$R$^8$, CH$_2$NR$^7$R$^8$, SO$_2$R$^d$, CH(OH)R$^{12}$, COR$^{12}$, CO$_2$R$^{12}$, CONR$^7$R$^8$, phenyl, heteroaryl, heteroarylC$_{1-4}$alkyl or CH$_2$OR$_{1-3}$, where said phenyl is optionally substituted by one or two substituents selected from C$_{1-4}$alkyl, C$_{1-4}$alkoxy, halogen or trifluoromethyl.

A further preferred class of compound of formula (I) is that wherein R$^9$ represents hydrogen, SO$_2$R$^d$ (in particular where R$^d$ is phenyl) or CONR$^7$R$^8$ (in particular where R$^7$ is C$_{1-4}$alkyl or C$_{2-4}$alkyl substituted by a hydroxyl or C$_{1-2}$alkoxy group and R$^8$ is hydrogen, C$_{1-4}$alkyl, C$_{1-4}$alkoxy or C$_{2-4}$alkyl substituted by a hydroxyl or C$_{1-2}$alkoxy group, or R$^7$ and R$^8$, together, with the nitrogen atom to which they are attached, form an azetidinyl, pyrrolidinyl, piperidinyl, morpholino, thiomorpholino, piperazino or piperazino group substituted on the nitrogen atom by a C$_{1-4}$alkyl, hydroxyC$_{1-2}$alkyl, C$_{1-4}$alkoxyC$_{1-2}$alkyl, phenyl or benzyl group).

Another preferred class of compounds of formula (I) is that wherein R$^{10}$ represents hydrogen, fluorine or hydroxy, and in particular that wherein R$^{10}$ is hydrogen.

Certain particularly apt compounds of the present invention include those wherein R$^3$ is a group selected from pyrrole, furan, thiene, pyridine, pyrazole, imidazole, oxazole, isoxazole, thiazole, isothiazole, pyrazine, pyrimidine, pyridazine, triazole, oxadiazole, thiadiazole, triazine, and tetrazole, each heteroaryl group being optionally substituted as previously defined.

Preferred compounds of the present invention are those wherein R$^3$ is a group selected from furan, pyridine, pyrazole, imidazole, oxazole, isoxazole, pyrazine, pyrimidine, thiazole, 1,2,3-triazole, 1,2,4-triazole, 1,2,4-oxadiazole, 1,3,4-oxadiazole and tetrazole, each heteroaryl group being optionally substituted as previously defined.

Particularly preferred compounds of the present invention are those wherein R$^3$ is a group selected from furan, pyridine, pyrimidine, 1,2,3-triazole, 1,2,4-triazole and tetrazole, each heteroaryl group being optionally substituted as previously defined.

An especially preferred class of compound of formula (I) is that wherein R$^3$ is the group where R$^{15}$ is hydrogen, halogen, C$_{1-6}$alkyl, C$_{1-6}$alkoxy, CF$_3$, OCF$_3$, NO$_2$, CN, SR$^a$, SOR$^a$, SO$_2$R$^a$, COR$^a$, CO$_2$R$^a$, (CH$_2$)$_r$CONR$^a$R$^b$, (CH$_2$)$_r$NR$^a$R$^b$ or (CH$_2$)$_r$NR$^a$COR$_b$, where R$^a$ and R$^b$ are hydrogen or C$_{1-4}$alkyl, and r is zero, 1 or 2.

The optionally substituted tetrazolyl group is particularly preferred.

$R^{15}$ is preferably hydrogen, $C_{1-4}$alkyl, especially methyl, $CF_3$, $(CH_2)_r CONR^a R^b$, $SOR^a$ or $SO_2 R^a$ where $R^a$, $R^b$ and r are as previously defined. Most especially, $R^{15}$ is $CF_3$.

One favoured group of compounds of the present invention are of the formula (Ia) and pharmaceutically acceptable salts thereof:

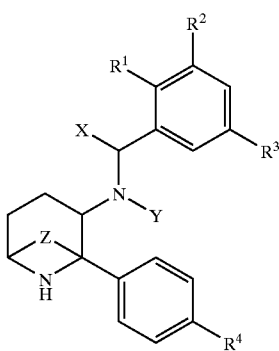
(Ia)

wherein $R^1$, $R^2$, $R^3$, $R^4$, X and Y are as defined in relation to formula (I) and Z is —$CR^9 R^{10} CH_2$—.

With respect to compounds of the formula (I), W (where present), may be a linear, branched or cyclic group. Favourably Y contains 1 to 4 carbon atoms and most favourably 1 or 2 carbon atoms. A particularly favourable group W is $CH_2$.

With respect to compounds of the formula (I), $R^7$ may aptly be a $C_{1-4}$alkyl group or a $C_{2-4}$alkyl group substituted by a hydroxyl or $C_{1-2}$alkoxy group, $R^8$ may aptly be hydrogen or a $C_{1-4}$alkyl group or a $C_{2-4}$alkyl group substituted by a hydroxyl or $C_{1-2}$alkoxy group, or $R^7$ and $R^8$ may be linked so that, together with the nitrogen atom to which they are attached, they form an azetidinyl, pyrrolidinyl, piperidyl, morpholino, thiomorpholino, piperazino or piperazino group substituted on the nitrogen atom by a $C_{1-4}$alkyl group or a $C_{2-4}$alkyl group substituted by a hydroxy or $C_{1-2}$alkoxy group.

Where the group $NR^7 R^8$ represents a heteroaliphatic ring of 4 to 7 ring atoms and said ring contains a double bond, a particularly preferred group is 3-pyrroline.

Where the group $NR^7 R^8$ represents a non-aromatic azabicyclic ring system, such a system may contain between 6 and 12, and preferably between 7 and 10, ring atoms. Suitable rings include 5-azabicyclo[2.1.1]hexyl, 5-azabicyclo[2.2.1]heptyl, 6-azabicyclo[3.2.1]octyl, 2-azabicyclo[2.2.2]octyl, 6-azabicyclo[3.2.2]nonyl, 6-azabicyclo[3.3.1]nonyl, 6-azabicyclo[3.2.2]decyl, 7-azabicyclo[4.3]decyl, 7-azabicyclo[4.4.1]undecyl and 8-azabicyclo[5.4.1]dodecyl, especially 5-azabicyclo[2.2.1]heptyl and 6-azabicyclo[3.2.1]octyl.

Where $R^8$ represents a $C_{2-4}$alkyl group substituted by a 4, 5 or 6 membered heteroaliphatic ring containing one or two heteroatoms selected from N, O and S, suitable rings include azetidinyl, pyrrolidino, piperidino, piperazino, morpholino, or thiomorpholino. Particularly preferred are nitrogen containing heteroaliphatic rings, especially pyrrolidino and morpholino rings.

Particularly suitable moieties —W—$NR^7 R^8$ include those wherein W is $CH_2$ or $CH_2 CH_2$ and $NR^7 R^8$ is amino, methylamino, dimethylamino, diethylamino, azetidinyl, pyrrolidino and morpholino.

In particular, W is preferably $CH_2$ and $NR^7 R^8$ is preferably dimethylamino, azetidinyl or pyrrolidino, especially dimethylamino.

When any variable occurs more than one time in formula (I) or in any substituent, its definition on each occurrence is independent of its definition at every other occurrence.

It will be appreciated that, where $R^9$ represents an oxo (=O) group, then $R^{10}$ will be absent and the group Z will in fact represent —C(O)CH$_2$— or —CH$_2$C(O)—.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

As used herein, the terms "fluoroC$_{1-6}$alkyl" and fluoroC$_{1-6}$alkoxy" mean a $C_{1-6}$alkyl or $C_{1-6}$alkoxy group in which one or more (in particular, 1 to 3) hydrogen atoms have been replaced by fluorine atoms. Similarly, the term "fluoroC$_{1-4}$alkyl" means a $C_{1-4}$alkyl group in which one or more (in particular 1 to 3) hydrogen atoms have been replaced by fluorine atoms. Particularly preferred are fluoroCi$_{1-3}$alkyl and fluoroC$_{1-3}$alkoxy groups, for example, $CF_3$, $CH_2 CH_2 F$, $CH_2 CHF_2$, $CH_2 CF_3$, $OCF_3$, $OCH_2 CH_2 F$, $OCH_2 CHF_2$ or $OCH_2 CF_3$, and most especially $CF_3$, $OCF_3$ and $OCH_2 CF_3$.

As used herein, the term "hydroxyC1alkyl" means a $C_{1-6}$alkyl group, in which one or more (in particular 1 to 3) hydrogen atoms have been replaced by a hydroxy group. Preferred are hydroxyC$_{1-3}$alkyl groups, especially where one hydrogen atom has been replaced by a hydroxy group, for example, $CH_2 OH$, $CH_2 CH_2 OH$ and $C(CH_3)_2 OH$.

The cycloalkyl groups referred to herein may represent, for example, cyclopropyl, cyclobutyl, cyclopentyl or cyclohexyl. A suitable cycloalkylalkyl group may be, for example, cyclopropylmethyl.

Similarly cycloalkoxy groups referred to herein may represent, for example, cyclopropoxy or cyclobutoxy.

As used herein, the terms "alkenyl" and "alkynyl" as a group or part of a group means that the group is straight or branched. Examples of suitable alkenyl groups include vinyl and allyl. A suitable alkynyl group is propargyl.

As used herein, the term "aryl" as a group or part of a group means a monocyclic, fused-bicyclic or linear bicyclic aromatic ring containing 6, or 12 carbon atoms, any of which rings is optionally substituted by one, two or three substituents selected from halogen, $C_{1-6}$alkyl, $C_{1-6}$alkoxy, or trifluoromethyl. Particular examples of such groups include phenyl, naphthyl and biphenyl. Phenyl is especially preferred.

As used herein, the term "heteroaryl" as a group or part of a group means a monocyclic or fused-bicyclic heteroaromatic ring containing between 5 and 10 ring members, of which 1 to 4 may be heteroatoms selected from N, O and S, and wherein any of which rings is optionally substituted by one or two substituents selected from halogen, $C_{1-4}$alkyl, $C_{1-6}$alkoxy, trifluoromethyl or phenyl. Particular examples of such groups include pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indole, benzofuran, benzthiophene, benzimidazole, benzoxazole and benzthiazole. Furanyl, thienyl, imidazolyl, oxazolyl, isoxazolyl, thiazolyl, triazolyl, tetrazolyl and pyridyl are particularly preferred. Where said rings are substituted, preferred substituents include methyl and phenyl groups.

When used herein the term "halogen" means fluorine, chlorine, bromine and iodine. The most apt halogens are fluorine and chlorine of which fluorine is preferred, unless otherwise stated.

Specific compounds within the scope of this invention include:

(1R*,2R*,5S*)-2-(3,5-bis(trifluoromethyl)benzylamino)-1-phenyl-8-azabicyclo[3.2.1]octane;

(1R*,2R*,5S*)-2-(2-methoxy-5-(trifluoromethoxy)benzylamino)-1-phenyl-8-azabicyclo[3.2.1]octane;

(1R*,2R*,5S*)-2-(2-cyclopropyloxy-5-[5-(trifluoromethyl)tetrazol-1-yl]benzylamino)-1-phenyl-8-azabicyclo[3.2.1]octane;

(1R*,2R*,5S*)-2-(2-methoxy-5-(trifluoromethoxy)benzylamino)-8-benzyl-1-phenyl-8-azabicyclo[3.2.1]octane;

(1R*,2R*,5S*)-2-(2-Cyclopropoxy-5-(trifluoromethoxy)-benzylamino)-1-phenyl-8-azabicyclo[3.2.1]octane;

(1R*,2R*,5S*,6R*)-2-(2-methoxy-5-(trifluoromethoxy)benzylamino)-1-phenyl-6-phenylsulphonyl-8-azabicyclo[3.2.1]octane;

(1R*,2R*,5S*,9S*)- and (1R*,2R*,5S*,9R*)-2-[1-(2-methoxy-5-(trifluoromethoxy)phenyl)ethylamino]-1-phenyl-8-azabicyclo[3.2.1]octane;

(1R*,2R*,5S*,6R*)-2-(2-cyclopropoxy-5-(trifluoromethoxy)-benzylamino)-6-30 (hydroxymethyl)-1-phenyl-8-azabicyclo[3.2.1]octane;

(1R*,2R*,5S*)-2-(2-chloro-5-(trifluoromethoxy)benzylamino)-1-phenyl-8-azabicyclo[3.2.1]octane (1R*,2R*,5S*,6R*)-2-(2-cyclopropoxy-5-(trifluoromethoxy)-benzylamino)-6-[1-(3-hydroxy)propyloxymethyl]-1-phenyl-8-azabicyclo[3.2.1]octane;

(1R*,2R*,5S*,6R*)-2-(2-cyclopropoxy-5-(trifluoromethoxy)-benzylamino)-6-(tert-butoxycarbonyl)-1-phenyl-8-azabicyclo[3.2.1]octane;

(1R*,2R*,5S*,6R*)-2-(2-cyclopropoxy-5-(trifluoromethoxy)-benzylamino)-6-(N-methoxy-N-methylcarboxamido)-1-phenyl-8-azabicyclo[3.2.1]octane;

(1R*,2R*,5S*,6R*)-2-(2-cyclopropoxy-5-(trifluoromethoxy)-benzylamino)-6-acetyl-1-phenyl-8-azabicyclo[3.2.1]octane;

(1R*,2R*,5S*,6R*,R*) and (1R*,2R*,5S*,6R*,S*)-2-(2-cyclopropoxy-5-(trifluoromethoxy)benzylamino)-6-(1-hydroxy)ethyl-1-phenyl-8-azabicyclo[3.2.1]octane;

(1R*,2R*,5S*,6R*)-2-(2-cyclopropoxy-5-(trifluoromethoxy)-benzylamino)-6-(1-hydroxy-1-methyl)ethyl-1-phenyl-8-azabicyclo[3.2.1]octane;

(1R*,2R*,5S*,6S*)-2-(2-cyclopropoxy-5-(trifluoromethoxy)-benzylamino)-6-(1H-tetrazol-5-yl)-1-phenyl-8-azabicyclo[3.2.1]octane;

(1R*,2R*,5S*,6S*)-2-(2-cyclopropoxy-5-(trifluoromethoxy)-benzylamino)-1-phenyl-6-(1-methyl-1H-tetrazol-5-yl)-8-azabicyclo[3.2.1]octane;

(1R*,2R*,5S*,6S*)-2-(2-cyclopropoxy-5-(trifluoromethoxy)-benzylamino)-1-phenyl-6-(2-methyl-2H-tetrazol-5-yl)-8-azabicyclo[3.2.1]octane;

(1R*,2R*,3S*,5S*,6R*)-2-(2-cyclopropoxy-5-(trifluoromethoxy)-benzylamino)-3-fluoro-1-phenyl-6-(hydroxymethyl)-8-azabicyclo[3.2.1]octane;

(1R*,2R*,5S*,6R*)-6-(bromomethyl)-2-(2-cyclopropoxy-5-(trifluoromethoxy)benzylamino)-1-phenyl-8-azabicyclo[3.2.1]octane;

(1R*,2R*,5S*,6R*)-2-(2-cyclopropoxy-5-(trifluoromethoxy)-benzylamino)-6-[(methylsulphonyl)methyl]-1-phenyl-8-azabicyclo[3.2.1]octane;

and pharmaceutically acceptable salts thereof.

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention have at least three asymmetric centres, and may accordingly exist both as enantiomers and as diastereoisomers. It is to be understood that all such isomers and mixtures thereof are encompassed within the scope of the present invention.

The preferred compounds of formula (I) and (Ia) will have the stereochemistry of the 1, 2 and 5 positions as possessed by, for instance, the compound of Example 1, i.e. as shown in formula (Ib)

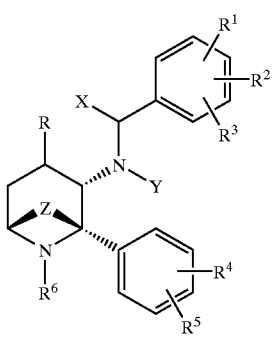

(Ib)

It will be appreciated that the preferred definitions of the various substituents recited herein may be taken alone or in combination and, unless otherwise stated, apply to the generic formula for compounds of the present invention as well as to the preferred class of compound represented by formula (Ia).

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, solutions or suspensions, or suppositories, for oral, parenteral or rectal administration, or administration by inhalation or insufflation. Oral compositions such as tablets, pills, capsules or wafers are particularly preferred.

A more detailed description of pharmaceutical compositions that are suitable for the formulation of compounds of the present invention is disclosed in U.S. Pat. No. 6,071,927, the content of which is incorporated herein by reference (see in particular, column 8, line 50 to column 10, line 4).

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. A comprehensive listing of clinical conditions, uses and methods of treatment for which the compounds of the present invention will be useful is disclosed in U.S. Pat. No. 6,071,927, the content of which is incorporated herein by reference (see, in particular, column 10, line 14 to column 22, line 18).

In particular, the compounds of the present invention are useful in the treatment of a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; and anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders.

The compounds of the present invention are also particularly useful in the treatment of nociception and pain. Diseases and conditions in which pain predominates, include soft tissue and peripheral damage, such as acute trauma, osteoarthritis, rheumatoid arthritis, musculo-skeletal pain, particularly after trauma, spinal pain, myofascial pain syndromes, headache, migraine, episiotomy pain, and burns.

The compounds of the present invention are also particularly useful in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; in the treatment of inflammatory diseases such as inflammatory bowel disease, psoriasis, fibrositis, osteoarthritis, rheumatoid arthritis, pruritis and sunburn; and in the treatment of allergic disorders such as eczema and rhinitis.

The compounds of the present invention are also particularly useful in the treatment of gastrointestinal (GI) disorders, including inflammatory disorders and diseases of the GI tract such as ulcerative colitis, Crohn's disease and irritable bowel syndrome.

The compounds of the present invention are also particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents, including those routinely used in cancer chemotherapy; by radiation including radiation therapy such as in the treatment of cancer; and in the treatment of post-operative nausea and vomiting.

The excellent pharmacological profile of the compounds of the present invention offers the opportunity for their use in therapy at low doses thereby minimizing the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

In the treatment of psychiatric disorders, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

As used herein, the term "treatment" includes prophylactic use to prevent the occurrence or recurrence of any of the aforementioned conditions.

According to a general process (A), compounds of formula (I) may be prepared by a process (A) which comprises reacting a compound of formula (II) with a compound of formula (III):

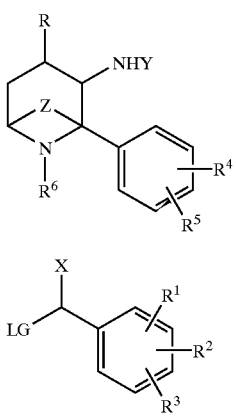

(II)

(III)

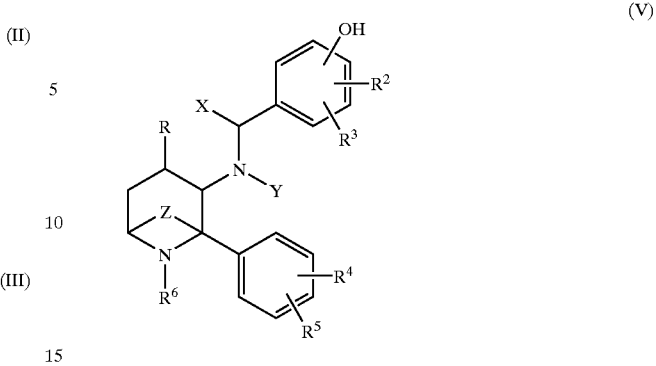

(V)

wherein R, R$^1$, R$^2$, R$^3$, R$^4$, R$^5$, R$^6$, X, Y and Z are as defined for formula (I), except that any reactive moiety is protected by a suitable protecting group; and LG represents a leaving group; in the presence of a base, followed by deprotection, if required.

Suitable leaving groups include halogen atoms, e.g. chlorine, bromine or iodine, or sulphonate derivatives such as tosylate, mesylate or triflate.

The reaction is conveniently carried out in a suitable organic solvent, such as an ether, e.g. 1,2-dimethoxyethane, at a temperature in the region of 0° C. Favoured bases of use in the reaction include alkali metal amides and hydrides, such as potassium bis(trimethylsilyl)amide or potassium hydride. Suitably, sodium hydride is used.

According to another general process (B), compounds of formula (I) may be prepared by the reductive amination of a compound of formula (II) with a compound of formula (IV), in the presence of a reducing agent:

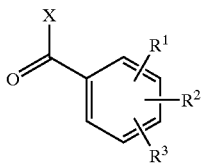

(IV)

Suitable reducing agents for use in this reaction include, for example, sodium cyanoborohydride or sodium triacetoxyborohydride, or catalytic hydrogenation. The reaction is conveniently effected in a suitable solvent such as acetic acid or methanol at a temperature between 0° C. and 50° C., conveniently at about room temperature.

According to another general process (C), compounds of formula (I) wherein R$^1$ is C$_{1-6}$alkoxy, fluoroC$_{1-6}$alkoxy, C$_{2-6}$alkenoxy, C$_{3-7}$cycloalkoxy, C$_{3-7}$cycloalkylC$_{1-4}$alkoxy or benzyloxy, may-be prepared by the interconversion of a compound of formula (I) wherein R$^1$ is hydroxy, hereinafter referred to as formula (V)

by reaction with an appropriate alkyl-, fluoroalkyl-, alkenyl-, cycloalkyl-, cycloalkylalkyl- or aralkyl-halide, especially the iodide, in the presence of a base.

Suitable bases include alkali metal hydrides, such as sodium hydride, in a suitable solvent such as dimethylformamide. The reaction is conveniently effected at about room temperature.

According to another general process (D), compounds of formula (I) may be prepared by the interconversion of a corresponding compound of formula (I) in which R$^6$ is H, hereinafter referred to as formula (VI)

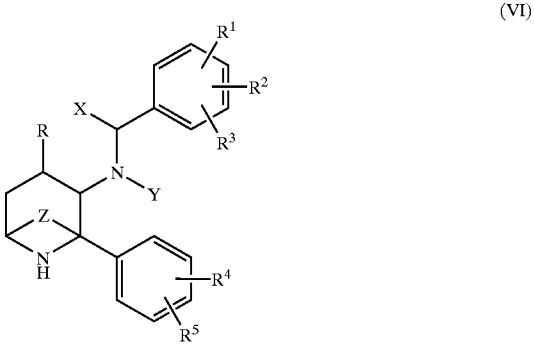

(VI)

by reaction with a compound of formula (VII):

LG—R$^{6a}$ (VII)

where R$^{6a}$ is a group of the formula R$^6$ as defined in relation to formula (I) (other than H) or a precursor therefor and LG is a leaving group such as an alky- or arylsulphonyloxy group (e.g. mesylate or tosylate) or a halogen atom (e.g. bromine, chlorine or iodine); and, if R$^{6a}$ is a precursor group, converting it to a group R$^6$ (in which process any reactive group may be protected and thereafter deprotected if desired).

This reaction may be performed in conventional manner, for example in an organic solvent such as dimethylformamide in the presence of an acid acceptor such as potassium carbonate.

Suitable alternative methods for introducing the group R$^6$ are described, for instance, in International Patent Specification No. WO 95/18124.

According to another general process (E), compounds of formula (I) may be prepared from a compound of formula (VIII)

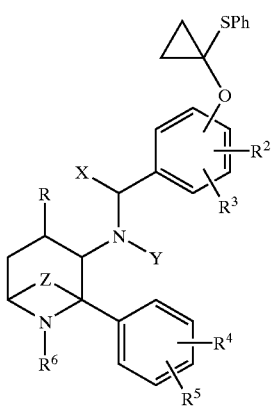

(VIII)

by either
(a) reaction with lithium naphthalenide in tetrahydrofuran, the reaction being effected at reduced temperature, for example at about −78° C.; or
(b) in a first step, oxidation of the phenylthio moiety using, for example, oxone in the presence of aluminium oxide, the reaction being effected in a suitable solvent such as a halogenated hydrocarbon, for example, chloroform, and conveniently at room temperature, and in a second step, removal of the phenylsulfonyl moiety using, for example, sodium amalgam in the presence of disodium hydrogen orthophosphonate, the reaction being effected in a suitable solvent such as an alcohol, for example, methanol, and at a reduced temperature, for example, between 0° C. and 10° C.

Further details of suitable procedures will be found in the accompanying Examples.

Compounds of formula (II) in which $R^{30}$ is NHY may be prepared, for example, by reaction of a compound of formula (IX)

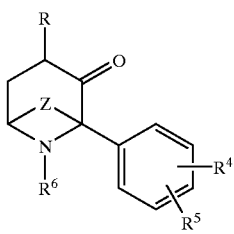

(IX)

with an amine of the formula $NHYR^{40}$ where $R^{40}$ is a hydrogen atom or, more preferably, an N-protecting group such as a benzyl group. The reaction is conveniently effected in two steps, firstly reacting the compound of formula (IX) with the amine, ideally in the presence of a suitable catalyst such as p-toluenesulfonic acid in a suitable solvent such as an aromatic hydrocarbon, for example, toluene, followed by treatment with a reducing agent such as a borohydride, for example, sodium cyanoborohydride, sodium triacetoxyborohydride or sodium borohydride. This second step is conveniently effected in a suitable solvent such as an alcohol, for example, methanol.

Where present, any N-protecting group may be removed by conventional procedures well known to the skilled worker (for instance, by catalytic hydrogenation in the presence of a suitable catalyst, for example, palladium on carbon, in a suitable solvent, such as acetic acid or methanol or a mixture thereof).

Compounds of formula (VIII) may be prepared from a compound of formula (V) by reaction with (1-iodo-cycloprop-1-yl)phenylsulfide.

Compounds of formula (IX) may be prepared from a compound of formula (X)

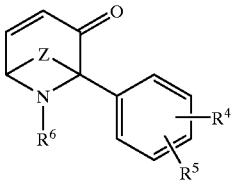

(X)

by catalytic hydrogenation using a metal catalyst such as palladium or platinum or hydroxides or oxides thereof, preferably in a suitable solvent such as alcohol, for example, methanol or ethanol, or an ester, for example, ethyl acetate, or an organic acid, for example, acetic acid, or a mixture thereof.

Compounds of formula (IX) wherein R is fluorine may be prepared by interconversion of a corresponding compound or formula (IX) in which R is hydrogen, using conventional fluorination techniques, for example, by treatment with lithium hexamethyldisilazide, followed by reaction with N-fluorobenzenesulfonamide.

Compounds of formula (X) wherein $R^6$ is benzyl or allyl, may be prepared from a compound of formula (XI)

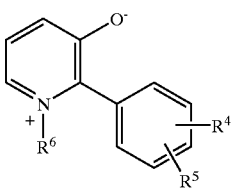

(XI)

(or a corresponding compound wherein the O⁻ is OH, and the compound is associated with a counterion, such as a bromide or chloride ion) by reaction with a vinyl compound of the formula $R^9CH=CH_2$, in particular where $R^9$ is cyano, $SO_2R^{13}$ (especially where $R^{13}$ is phenyl) or $CO_2R^{13}$ (especially where $R^{13}$ is tert-butyl), in the presence of an organic base such as a trialkylamine, for example, triethylamine. The reaction is conveniently effected in an aprotic solvent such as an aromatic hydrocarbon, for example, toluene.

The reaction of a compound of formula (XI) with acrylonitrile is particularly suitable for preparing compounds where the $R^9$ substituent is situated on either of the carbon atoms of the two-carbon bridge.

In a preferred embodiment of the aforementioned processes, $R^6$ is a benzyl group. The various reduction reactions described above may conveniently replace the benzyl group with a hydrogen atom. It will be appreciated from the discussion above that compounds of formula (I) wherein $R^6$ is a hydrogen atom are particularly preferred precursors to other compounds of formula (I).

Compounds of formula (III) and (IV) are either known compounds or may be prepared by methods analogous to those described herein.

It will be appreciated that the general methodology described above may be adapted, using methods that are readily apparent to one of ordinary skill in the art, in order to prepare further compounds of the present invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with $IC_{50}$ at the human $NK_1$ receptor of less than 100 nM on said test method.

The following non-limiting Examples serve to illustrate the preparation of compounds of the present invention:

DESCRIPTION 1

N-Benzyl-3-hydroxy-2-phenylpyridinium Bromide

A suspension of 3-hydroxy-2-phenylpyridine (20 g, 116 mmol) in toluene (250 ml) was heated at reflux for 30 minutes. Benzyl bromide (20 ml) was added and the reaction mixture was heated at reflux for 6 hours then cooled using an ice bath. The solid residue was collected by filtration and washed twice with ether to give crude N-benzyl-3-hydroxy-2-phenylpyridinium bromide (36.5 g, 91%) which was used in the next step without further purification.

$\delta_H$ (360 MHz, $CDCl_3$): 11.88 (1H, s), 9.47 (1H, d, J 7.2 Hz), 8.16 (1H, d, J 8.1 Hz), 8.05 (1H, dd, J 6.0 Hz, 8.8 Hz), 7.60–7.45 (3H, m), 7.37–7.22 (5H, m), 6.88 (2H, dd, J 6.2 Hz, 7.9 Hz), 5.61 (2H, s).

DESCRIPTION 2

(1R*,5S*,6R*)-8-Benzyl-1-phenyl-6-phenylsulphonyl-8-azabicyclo[3.2.1]oct-3-en-2-one A mixture of N-benzyl-3-hydroxy-2-phenylpyridinium bromide (Description 1; 4.91 g, 14.3 mmol), phenyl vinyl sulphone (4.2 g, 25 mmol), triethylamine (2.8 ml, 20 mmol) and 1,4-dioxane (50 ml) was heated at reflux overnight. After cooling to room temperature, the reaction mixture was poured onto saturated aqueous $NaHCO_3$ and extracted with ethyl acetate (3×100 ml). The combined organic extracts were dried ($Na_2SO_4$) and concentrated. The residue was purified by chromatography on silica gel (iso-hexane:diethyl ether 10–70%) to give the title compound (4.84 g, 78%) as a yellow-orange foam. Crystallisation from iso-hexane:diethyl ether gave the title compound as yellow rhombs.

$\delta_H$ (360 MHz, $CDCl_3$): 7.75–7.60 (5H, m), 7.48 (2H, t, J 7.7 Hz), 7.41–7.25 (8H, m), 6.86 (1H, dd, J 4.8 Hz, 9.6 Hz), 6.23 (1H, d, J 9.6 Hz), 4.25 (1H, d, J 4.8 Hz), 3.65 (1H, d, J 13.4 Hz), 3.56 (1H, dd, J 4.0 Hz, 9.4 Hz), 3.43 (1H, d, J 13.5 Hz), 2.83 (1H, dd, J 3.9 Hz, 14.9 Hz), 2.56 (1H, dd, J 9.4 Hz, 15.0 Hz).

DESCRIPTION 3

(1R*,5S*,6R*)-8-Benzyl-1-phenyl-6-phenylsulphonyl-8-azabicyclo[3.2.1]octan-2-one 10% Palladium on carbon (1 g) was added as a slurry in water (2 ml) to a solution of (1R*,5S*,6R*)-8-benzyl-1-phenyl-6-phenylsulphonyl-8-azabicyclo[3.2.1]oct-3-ene-2-one (Description 2; 11 g, 25.6 mmol) in methanol (50 ml) and ethyl acetate (50 ml). The mixture was hydrogenated at 30psi for one hour. The reaction mixture was filtered through a pad of Celite™. The filter cake was washed with dichloromethane (1L) and the combined filtrates concentrated in vacuo to give the title compound (10.8 g, 98%).

$\delta_H$ (400 MHz, $CDCl_3$): 7.79 (2H, d, J 7.2 Hz), 7.68 (1H, t, J 6.4 Hz), 7.51 (2H t, J 7.6 Hz), 7.41–7.25 (10H, m), 3.94 (1H, br s), 3.73–3.69 (1H, d, J 14.0 Hz), 3.63 (1H, t, J 7.7 Hz), 3.36 (1H, d, J 14.0 Hz), 2.71–2.54 (5H, m), 1.77 (1H, m).

DESCRIPTION 4

(1R*,2R*,5S*,6R*)-2-Benzylamino-8-benzyl-1-phenyl-6-phenylsulphonyl-8-azabicyclo[3.2.1]octane A mixture of (1R*,5S*,6R*)-8-benzyl-1-phenyl-6-phenylsulphonyl-8-azabicyclo[3.2.1]octan-2-one (Description 3; 15.0 g, 35 mmol), p-toluenesulfonic acid monohydrate (50 mg) and benzylamine (5.5 g, 51 mmol) in toluene (150 mL) was heated at reflux under Dean Stark conditions for 24 hours, then cooled and the solvent removed in vacuo.

The residue was dissolved in methanol (300 mL) and sodium cyanoborohydride (2.3 g, 36 mmol) added. The solution formed was stirred at room temperature for 16 hours then concentrated to approximately ¼ volume. Saturated aqueous sodium hydrogen carbonate solution (500 mL) was added and the suspension formed was extracted with ethyl acetate (2×500 mL). The extracts were dried ($MgSO_4$) and concentrated, before the residue was purified by silica chromatography to give the title compound as a gum.

$\delta_H$ (400 MHz, $CDCl_3$): 7.65–7.63 (2H, m), 7.59–7.55 (1H, m), 7.50–7.48 (2H, m), 7.41–7.37 (4H, m), 7.32–7.21 (11H, m), 4.34 (1H, d, J 14.6 Hz), 3.90 (1H, d, J 13.5 Hz), 3.82 (1H, m), 3.68–3.63 (2H, m), 3.48 (1H, dd, J 5.6 Hz and 9.1 Hz), 3.25 (1H, d, J 3.5 Hz), 2.36–2.23 (3H, m), 2.04–2.00 (1H, m), 1.72—1.76 (1H, m), 0.98–1.00 (1H, m). MS ($ES^+$) 523 (M+H).

DESCRIPTION 5

(1R*,2R*,5S*,6R*)-2-amino-1-phenyl-6-phenylsulphonyl-8-azabicyclo[3.2.1]octane (1R*,2R*,5S*,6R*)-2-benzylamino-8-benzyl-1-phenyl-6-phenylsulphonyl-8-azabicyclo[3.2.1]octane (Description 4; 1.73 g, 3.3 mmol) was dissolved in a mixture of methanol (30 mL) and acetic acid (20 mL), then treated with 10% palladium on charcoal (500 mg). The suspension was hydrogenated at 50 psi hydrogen for 16 hours, then filtered and concentrated. The residue was basified with saturated sodium bicarbonate solution (100 mL) and extracted with dichloromethane (2×100 mL). The extracts were dried ($MgSO_4$) and concentrated, and the residue purified by silica chromatography to give the title compound as a gum (1.10 g, 3.2 mmol).

$\delta_H$ (400 MHz, $CDCl_3$): 7.87–7.85 (2H, m), 7.68–7.63 (1H, m), 7.58–7.53 (2H, m), 7.36–7.20 (5H, m), 4.05 (1H, t, J 2.8 Hz), 3.60 (1H, dd, J 5.0 Hz and 8.8 Hz), 2.82 (1H, dd, J 1.6 Hz and 4.7 Hz), 2.55 (1H, dd, J 8.8 Hz and 14.2 Hz), 2.30 (1H, dd, J 5.0 Hz and 14.2 Hz), 1.96–1.64 (6H, m), 1.38–1.25 (1H, m). MS ($ES^+$) 343 (M+H).

DESCRIPTION 6

(1R*,2R*,5S*)-2-amino-1-phenyl-8-azabicyclo[3.2.1]octane (1R*,2R*,5S*,6R*)-2-amino-1-phenyl-6-phenylsulphonyl-8-azabicyclo[3.2.1]octane (Description 5; 1.0 g, 2.9 mmol) in methanol (20 mL) was treated with disodium hydrogen phosphate (1.65 g, 11.6 mmol) and 10% sodium amalgam (2.67 g), and the mixture stirred for 40 minutes. Saturated sodium bicarbonate solution (100 mL) was then added and the suspension extracted with dichloromethane (2×100 mL). The extracts were dried (MgSO$_4$) and concentrated, and the residue purified by silica chromatography to give the title compound as a gum (315 mg, 1.6 mmol).

$\delta_H$ (400 MHz, CDCl$_3$): 7.37–7.18 (5H, m), 3.69–3.67 (1H, m), 3.00 (1H, dd, J 1.4 Hz and 4.5 Hz), 2.30–2.22 (1H, m), 2.14–1.65 (8H, m), 1.58–1.52 (1H, m), 1.37–1.33 (1H, m). MS (ES$^+$) 203 (M+H).

DESCRIPTION 7

2-Methoxy-5-(trifluoromethoxy)benzaldehyde

To 4-(trifluoromethoxy)anisole (5.0 g, 26 mmol) in tetrahydrofuran (100 mL) cooled to −78° C. was slowly added a solution of tert-butyllithium in pentanes (23 mL, 1.7M, 39 mmol). The resulting solution was stirred at −78° C. for 30 minutes, before N,N'-dimethylformamide (8 mL, 104 mmol) was added. The solution was allowed to stir to ambient temperature and was then quenched with saturated aqueous ammonium chloride (100 mL). The suspension formed was extracted with ethyl acetate (2×100 mL) and the extracts dried (MgSO$_4$). Concentration gave a yellow oil which was purified by silica chromatography to give the title compound as an oil (4.13 g, 18.8 mmol).

$\delta_H$ (360 MHz, CDCl$_{13}$): 10.43 (1H, s), 7.69 (1H, d, J 3.1 Hz), 7.40 (1H, dd, J 3.1 and 9.1 Hz), 7.01 (1H, d, J 9.1 Hz), 3.96 (3H, s).

DESCRIPTION 8

(1R*,2R*,5S*,6R*)-2-amino-8-benzyl-1-phenyl-6-phenylsulphonyl-8-azabicyclo[3.2.1]octane (1R*,2R*,5S*,6R*)-2-benzylamino-8-benzyl-1-phenyl-6-phenylsulphonyl-8-azabicyclo[3.2.1]octane (Description 4; 8.34 g, 16 mmol) was dissolved in methanol (150 mL) and acetic acid (150 mL), then treated with 10% palladium on activated charcoal (2 g). The suspension was then hydrogenated at 50 psi hydrogen for 16 hours, then filtered. The filtrate was concentrated in vacuo, and the oil remaining suspended in saturated aqueous sodium hydrogen carbonate solution (250 mL). This was extracted with ethyl acetate (2×250 mL) and the extracts were dried (MgSO$_4$), then concentrated. Purification by silica chromatography yielded the title compound as a gum (3.37 g, 7.8 mmol).

$\delta_H$ (360 MHz, D$_6$-DMSO): 7.73–7.67 (3H, m), 7.57–7.48 (5H, m), 7.39–7.35 (4H, m), 7.29–7.17 (3H, m), 4.36 (1H, d, J 15.4 Hz), 3.90 (1H, dd, J 5.4 and 9.2 Hz), 3.69 (1H, d, J 15.4 Hz), 3.55 (2H, s), 2.30–1.98 (4H, m), 1.61–1.57 (2H, m), 0.93–0.90 (1H, m). MS (ES$^+$) 433 (M+H).

DESCRIPTION 9

(1R*,2R*,5S*)-2-amino-8-benzyl-1-phenyl-8-azabicyclo[3.2.1]octane

Lithium (175 mg, 25 mmol) was added to a solution of naphthalene (3.2 g, 25 mmol) in tetrahydrofuran (25 mL), and the mixture sonicated for 2 hours. The green solution formed was then slowly added to a solution of (1R*,2R*,5S*,6R*)-2-amino-8-benzyl-1-phenyl-6-phenylsulphonyl-8-azabicyclo[3.2.1]octane (Description 8; 2.0 g, 4.6 mmol) in tetrahydrofuran (50 mL), already cooled to −78° C. The mixture was stirred at −78° C. for 1 hour, then quenched with aqueous saturated ammonium chloride solution (50mL). After warming to ambient temperature, the mixture was extracted with ethyl acetate (2×100 mL) and the extracts dried (MgSO$_4$). Concentration in vacuo yielded a solid, which was purified by silica chromatography to give the title compound as a gum (900 mg, 3.1 mmol).

$\delta_H$ (360 MHz, CDCl$_3$): 7.45–7.43 (2H, m), 7.35–7.18 (8H, m), 3.98 (1H, d, J 15.1 Hz), 3.27 (1H, t, J 2.8 Hz), 3.00 (1H, d, J 15.1 Hz), 2.52 (1H, d, J 3.6 Hz), 2.33–2.14 (3H, m), 2.06–1.86 (3H, m), 1.74–1.60 (3H, m), 1.34–1.25 (1H, MS (ES$^+$) 293 (M+H).

DESCRIPTION 10

1-(2-Chloroethoxy)-2-iodo-4-(trifluoromethoxy)benzene

2-Iodo-4-(trifluoromethoxy)phenol (10 g, 33 mmol), 2-chloroethyl-p-toluenesulfonate (7.9 g, 34 mmol), N,N'-dimethylformamide (50 mL) and potassium carbonate (9.1 g, 66 mmol) were stirred together at 50° C. for 16 hours and then cooled. The suspension was diluted with water (100 mL) and extracted with 60% diethyl ether/hexane (2×100 mL). The extracts were dried (MgSO$_4$) and concentrated to give the title compound as a solid (12.1 g, 33 mmol).

$\delta_H$ (360 MHz, CDCl$_3$): 6.43 (1H, d, J 2.6 Hz), 5.96 (1H, dd, J 2.6 and 9.0 Hz), 5.57 (1H, d, J 9.0 Hz), 3.04 (2H, t, J 6.0 Hz), 2.64 (2H, t, J 6.0 Hz).

DESCRIPTION 11

1-(Vinyloxy)-2-iodo-4-(trifluoromethoxy)benzene

To 1-(2-chloroethoxy)-2-iodo-4-(trifluoromethoxy)benzene (Description 10; 12.1 g, 33 mmol) in tetrahydrofuran (50 mL) at −5° C. was slowly added potassium tert-butoxide (3.7 g, 33 mmol). After addition was complete, the solution was allowed to stir to room temperature for 20 hours, and was then quenched with water (100 mL). The mixture was extracted with 50% diethyl ether/hexane (2×100 mL) and the extracts dried (MgSO$_4$). Concentration gave an oil which was purified by silica chromatography to give the title compound as an oil (7.62 g, 23 mmol).

$\delta_H$ (360 MHz, CDCl$_3$): 7.67 (1H, d, J 2.6 Hz), 7.20 (1H, dd, J 2.6 and 8.8 Hz), 6.96 (1H, d, J 8.8 Hz), 6.54 (1H, dd, J 6.0 and 13.7 Hz), 4.80 (1H, dd, J 2.1 and 13.7 Hz), 4.56 (1H, dd, J 2.1 and 6.9 Hz).

DESCRIPTION 12

1-(Cyclopropoxy)-2-iodo-4-(trifluoromethoxy)benzene 1-(Vinyloxy)-2-iodo-4-(trifluoromethoxy)benzene (Description 11; 7.6 g, 23 mmol) and chloroiodomethane (5.4 mL, 74 mmol) were dissolved in 1,2-dichloroethane (40 mL) and cooled to 0° C. Diethyl zinc (3.8 mL, 36.8 mmol) was then added dropwise. The solution was allowed to warm to room temperature for 10 minutes, then cooled back to 0° C. when it was quenched with saturated aqueous ammonium chloride solution (50 mL). The suspension formed was extracted with 50% diethyl ether/hexane (2×100 mL) and the extracts dried (MgSO$_4$). Concentration yielded a yellow oil which was purified by silica chromatography to give the title compound as a clear oil (5.84 g, 17 mmol).

$\delta_H$ (400 MHz, CDCl$_3$): 7.62 (1H, d, J 2.8 Hz), 7.20 (1H, dd, J 2.8 and 9.0 Hz), 6.96 (1H, d, J 9.0 Hz), 3.81–3.77 (1H, m), 0.86–0.83 (4H, m).

DESCRIPTION 13

2-(Cyclopropoxy)-5-(trifluoromethoxy)benzaldehyde 1-(Cyclopropoxy)-2-iodo-4-(trifluoromethoxy)benzene (Description 12; 5.84 g, 17 mmol) was dissolved in tetrahydrofuran (150 mL) and cooled to −78° C. Tert-butyl lithium solution (20 mL, 1.7M in pentanes, 34 mmol) was then added dropwise. The solution was stirred at −78° C. for 10 minutes, before N,N'-dimethylformamide (5.3 mL, 68 mmol) was added, and the resulting solution allowed to stir to room temperature. Saturated aqueous ammonium chloride solution (50 mL) was then added and the mixture extracted with diethyl ether (2×100 mL). The extracts were dried (MgSO$_4$) and concentrated to yield an oil. Purification of this by silica chromatography gave the title compound as a clear oil (3.94 g, 16 mmol).

$\delta_H$ (360 MHz, CDCl$_3$): 10.34 (1H, s), 7.67–7.66 (1H, m), 7.42–7.37 (2H, m), 3.88–3.83 (1H, m), 0.90–0.87 (4H, m).

DESCRIPTION 14

1-Hydroxy-1-(2-methoxy-5-(triflouromethoxy)phenyl)ethane

To 2-methoxy-5-(trifluoromethoxy)benzaldehyde (1.0 g, 4.5 mmol) in tetrahydrofuran (10 mL) at 0° C. was added a solution of methyl magnesium bromide in tetrahydrofuran (1.6 mL, 3M, 4.7 mmol). The solution was then warmed to room temperature and quenched with saturated aqueous ammonium chloride solution (50 mL). The suspension formed was extracted with ethyl acetate (2×100 mL) and the extracts were dried (MgSO$_4$). Concentration in vacuo yielded the title compound as an oil (1.03 g, 4.4 mmol).

$\delta_H$ (360 MHz, CDCl$_3$): 7.25 (1H, d, J 2.0 Hz), 7.09 (1H, dd, J 2.0 and 8.9 Hz), 6.84 (1H, d, J 8.9 Hz), 5.10 (1H, dq, J 4.8 and 6.5 Hz), 3.86 (3H, s), 2.41 (1H d, J 4.8 Hz), 1.48 (3H, d, J 6.5 Hz).

DESCRIPTION 15

2-Methoxy-5-(triflouromethoxy)acetophenone

1-Hydroxy-1-(2-methoxy-5-(triflouromethoxy)phenyl) ethane (Description 14; 1.03 g, 4.4 mmol) in dichloromethane (20 mL) was treated with 1,1,1-triacetoxy-1,1-dihydro-1,2-benziodoxol-3(1H)-one (1.85 g, 4.4 mmol) and stirred at room temperature for 15 minutes. Aqueous sodium metabisulphite solution (10 mL) was added and the solution was stirred for 10 minutes. The organic layer was removed, washed with water, brine, then dried (MgSO$_4$). Concentration gave an oil which was purified by silica chromatography to yield the title compound as a waxy solid (840 mg, 3.6 mmol).

$\delta_H$ (360 MHz, CDCl): 7.62 (1H, d, J 2.1 Hz), 7.31 (1H, dd, J 2.1 and 9.0 Hz), 6.97 (1H, d, J 9.0 Hz), 3.93 (3H, s), 2.62 (3H, s).

DESCRIPTION 16

(1R*,5S*,6RS)-8-Benzyl-6-(tert-butoxycarbonyl)-1-phenyl-8-azabicyclo[3.2.1]oct-3-en-2-one A mixture of N-benzyl-3-hydroxy-2-phenylpyridinium bromide (255 g, 0.745 mol), tert-butyl acrylate (470 ml), triethylamine (150 ml) and 1,4-dioxane (1 l) was heated at reflux for 15 hours and cooled to room temperature. The reaction mixture was poured onto saturated aqueous NaHCO$_3$ (1 l) and extracted into an 1:1 mixture of iso-hexane:diethyl ether (3×500 ml). The combined organic extracts were dried (Na$_2$SO$_4$) and concentrated. The residue was purified by chromatography on silica gel (750 g, iso-hexane:diethyl ether 0–20%) to give a 2:1 mixture of (1R*,5S*,6R*)-8-benzyl-6-(tert-butoxycarbonyl)-1-phenyl-8-azabicyclo[3.2.1]oct-3-en-2-one and (1R*,5S*,6S*)-8-benzyl-6-(tert-butoxycarbonyl)-1-phenyl-8-azabicyclo[3.2.1]oct-3-en-2-one (205 g, 70%) as a yellow-orange foam. The isomers were separated on silica gel (iso-hexane:diethyl ether) and crystallised from iso-hexane:diethyl ether giving yellow rhombs:

DESCRIPTION 16a (1R*,5S*,6R*)-8-Benzyl-6-(tert-butoxycarbonyl)-1-phenyl-8-azabicyclo[3.2.1]oct-3-en-2-one $\delta_H$ (360 MHz, CDCl$_3$): 7.83 (1H, dd, J 1.4 Hz, 8.6 Hz), 7.40–7.25 (8H, m), 6.91 (1H, dd, J 4.8 Hz, 9.7 Hz), 6.18 (1H, d, J 9.7 Hz), 4.10 (1H, d, J 4.8 Hz), 3.67 (1H, d, J 13.0 Hz), 3.51 (1H, d, J 14.0 Hz), 2.99 (1H, dd, J 2.6 Hz, 14.2 Hz), 2.84 (1H, dd, J 2.6 Hz, 9.0 Hz), 2.39 (1H, dd, J 9.0 Hz, 14.2 Hz), 1.43 (9H, s).

DESCRIPTION 16b: (1R*,5S*,6S*)-8-Benzyl-6-(tert-butoxycarbonyl)-1-phenyl-8-azabicyclo[3.2.1]oct-3-en-2-one $\delta_H$ (360 MHz, CDCl): 7.70 (1H, dd, J 1.3 Hz, 8.7 Hz), 7.40–7.25 (8H, m), 6.88 (1H, dd, J 4.8 Hz, 9.8 Hz), 6.25 (1H, d, J 9.8 Hz), 4.02 (1H, dd, J 5.0 Hz, 6.0 Hz), 3.65–3.50 (3H, m), 2.60 (2H, m), 1.43 (9H, s).

DESCRIPTION 17

(1R*,5S*,6RS)-8-Benzyl-6-(tert-butoxycarbbnyl)-1-phenyl-8-azabicyclo[3.2.1]octan-2-one A mixture of (1R*,5S*,6RS)-8-benzyl-6-(tert-butoxycarbonyl)-1-phenyl-8-azabicylco[3.2.1]oct-3-en-2-one (Description 16; 26 g, 66 mmol), 10% palladium on charcoal (3.5 g, 3.3 mmol), ethyl acetate (50 ml) and methanol (100 ml) was stirred under hydrogen atmosphere (1 atm) at room temperature for 1 hour. The reaction mixture was treated with dichloromethane (500 ml), filtered through a pad of Celite™. The filter cake was well washed with dichloromethane and the filtrate was concentrated to give the title compound as a solid (26 g, 100%). The isomers were separated on silica gel (iso-hexane:ethyl acetate) and crystallised from acetone:iso-hexane yielding pure ketones as a colourless crystals.

6R*-epimer: $\delta_H$ (360 MHz, CDCl$_3$): 7.50 (2H, dm, J 7.2 Hz), 7.41 (2H, d, J 7.3 Hz), 7.33 (4H, m), 7.25 (2H, m), 3.72 (1H, m), 3.70 (1H, d, J 15.0 Hz), 3.44 (1H, d, J 14.6 Hz), 2.91 (1H, dd, J 5.2 Hz, 9.5 Hz), 2.75–2.45 (5H, m), 1.97–1.87 (1H, m), 1.46 (9H, s). 6S*-epimer: OH (360 MHz, CDCl$_3$): 7.50–7.20 (10H, m), 3.75 (1H, d, J 14.7 Hz), 3.61 (1H, dd, J 3.5 Hz, 6.3 Hz), 3.52 (1H, d, J 14.8 Hz), 3.46 (1H, dt, J 6.7 Hz, 11.6 Hz), 2.95 (1H, m), 2.90 (1H, dd, J 7.0 Hz, 14.4 Hz), 2.53–2.36 (2H, m), 2.26 (1H, dd, J 11.6 Hz, 14.0 Hz), 1.94 (1H, d, J 14.0 Hz), 1.91 (1H, m), 1.46 (9H, s).

DESCRIPTION 18

(1R*,2R*,5S*,6R*)-2-Benzylamino-8-benzyl-6-(tert-butoxycarbonyl)-1-phenyl-8-azabicyclo[3.2.1] octane (1R*,5S*,6R*)-8-Benzyl-6-(tert-butoxycarbonyl)-1-phenyl-8-azabicyclo[3.2.1]octan-2-one (Description 17; 5.0 g, 12.8 mmol), p-toluenesulfonic acid monohydrate (25 mg) and benzylamine (2.1 g, 20 mmol) in toluene (50mL) was heated at reflux under Dean Stark conditions for 24 hours, then cooled and the solvent removed in vacuo. The residue was dissolved in methanol (100 mL) and sodium cyanoborohydride (900 mg, 14 mmol) added. The solution formed was stirred at room temperature for 2 hours then concentrated to approximately ¼ volume. Water (500 mL) was added and the suspension formed was extracted with ethyl acetate (2×500 mL). The extracts were dried ($MgSO_4$) and concentrated, before the residue was purified by silica chromatography to give the title compound (3.87 g, 8 mmol) as a gum.

$\delta_H$ (360 MHz, $CDCl_3$): 7.46–7.41 (3H, m), 7.30–7.19 (12H, m), 4.31 (1H, d, J 15.4 Hz) 3.86 (1H, d, J 13.6 Hz), 3.65–3.61 (3H, m), 3.08 (1H, d, J 3.1 Hz), 2.73–2.70 (1H, m), 2.47–2.41 (1H, m), 2.30–2.18 (1H, m), 2.15–2.07(1H, 2.03–1.94(1H, m), 1.88–1.76(1H, m), 1.41 (9H, s), 1.25–1.15 (1H, m). MS ($ES^+$) 483 (M+H).

DESCRIPTION 19

(1R*,2R*,5S*,6R*)-2-Benzylamino-8-benzyl-6-hydroxymethyl-1-phenyl-8-azabicyclo[3.2.1]octane (1R*,2R*,5S*,6R*)-2-Benzylamino-8-benzyl-6-(tert-butoxycarbonyl)-phenyl-8-azabicyclo[3.2.1]octane (Description 18; 600 mg, 1.2 mmol) in dichloromethane (10 mL) was cooled to −5° C. and a solution of diisobutylaluminium hydride in dichloromethane (3 mL, 1M, 3 mmol) was added dropwise. The solution was allowed to stir to ambient temperature over 2 hours, then dichloromethane (30 mL) was added followed by saturated aqueous potassium sodium tartrate solution (50 mL). The biphasic system was stirred vigorously for 1 hour, then the organic layer removed and dried ($MgSO_4$). Concentration in vacuo gave a gum which was purified by silica chromatography to yield the title compound (258 mg, 0.63 mmol).

$\delta_H$ (360 Mz, CDCl): 7.50–7.23 (15H, m), 4.48 (1H, d, J 14.1 Hz), 3.94 (1H, d, J 13.6 Hz), 3.77–3.50 (4H, m), 3.32 (1H, d, J 3.2 Hz), 3.26 (1H, s), 2.48–2.33 (1H, m), 2.15–1.72 (4H, m), 1.68–1.40 (2H, m), 1.11–1.07 (1H, m). MS ($ES^+$) 413 (M+H).

DESCRIPTION 20

(1R*,2R*,5S*,6R*)-2-Amino-6-hydroxymethyl-1-phenyl-8-azabicyclo[3.2.1]octane (1R*,2R*,5S*,6R*)-2-Benzylamino-8-benzyl-6-hydroxymethyl-1-phenyl-8-azabicyclo[3.2.1]octane (Description 19; 220 mg, 0.53 mmol) was dissolved in ethanol (5 mL) and treated with 10% palladium on activated charcoal (100 mg), followed by 1,4-cyclohexadiene (1.5 mL). The suspension formed was heated at reflux for 24 hours, then cooled and filtered. The filtrate was concentrated in vacuo, and the oil remaining purified by silica chromatography to yield the title compound as a gum (92 mg, 0.4 mmol).

$\delta_H$ (360 MHz, $CDCl_3$): 7.38–7.12 (5H, m), 3.72 (1H, dd, J 3.9 and 9.9 Hz), 3.56 (1H, s), 3.50 (1H, dd, J 4.8 and 9.9 Hz), 3.16 (1H, d, J 3.9 Hz), 2.41 (1H dd, J 9.0 and 13.1 Hz), 2.28–1.88 (4H, m), 1.77 (1H, dd, J 3.9 and 13.1 Hz), 1.59–1.54 (1H, m), 1.43–1.38 (1H, m). MS ($ES^+$) 233 (M+H).

DESCRIPTION 21

(1R*,2R*,5S*,6R*)-2-Dibenzylamino-8-benzyl-6-(hydroxycarbonyl)-1-phenyl-8-azabicyclo[3.2.1]octane (1R*,R2R*,5S*,6R*)-2-Benzylamino-8-benzyl-6-(tert-butoxycarbonyl)-1-phenyl-8-azabicyclo[3.2.1]octane (Description 18; 1.8 g, 3.7 mmol) was dissolved in N,N'-dimethylformamide (20 mL) and treated with potassium carbonate (966 mg, 7 mmol) and benzyl bromide (833µL, 7 mmol). The suspension was stirred at ambient temperature for 16 hours, then poured into water (200 mL). The mixture was extracted with ethyl acetate (2×100 mL) and the extracts were concentrated in vacuo, before being dissolved in 30% trifluoroacetic acid/dichloromethane (50 mL). This solution was stirred for 2 hours, concentrated, and the residue was basified with saturated aqueous sodium hydrogen carbonate solution (100 mL). The organics were extracted with dichloromethane (2×50 mL) and the extracts were dried ($MgSO_4$). The solid remaining was then purified by silica chromatography to give the acid as a white foam (400 mg, 0.8 mmol).

$\delta_H$ (360 MHz, $CDCl_3$): 7.37–7.02 (20H, m), 4.07 (1H, d, J 14.3 Hz), 3.91 (1H, s), 3.42–3.40 (2H, m), 3.02–2.92 (2H, m), 2.82 (1H, d, J 14.6 Hz), 2.43–2.10 (4H, m), 1.96–1.70 (4H, m). MS ($ES^+$) 518 (M+H).

DESCRIPTION 22

(1R*,2R*,5S*,6R*)-2-Dibenzylamino-8-benzyl-6-(hydroxymethyl)-1-phenyl-8-azabicyclo[3.2.1]octane (1R*,2R*,5S*,6R*)-2-Dibenzylamino-8-benzyl-6-(hydroxycarbonyl)-1-phenyl-8-azabicyclo[3.2.1]octane (Description 21; 400 mg, 0.78 mmol) was dissolved in tetrahydroftiran (10 mL) and treated with lithium aluminium hydride solution (800 µL, 1M, 0.8 mmol) in tetrahydrofuran. The resulting mixture was stirred for 16 hours, then a further portion of lithium aluminium hydride solution (200 µL, 1M, 0.8 mmol) in tetrahydrofuran was added. Stirred at 50° C. for 1 hour, then cooled, and water (40 µL) added, followed by 15% aqueous sodium hydroxide solution (40 µL), then water (120 µL). The suspension formed was filtered and the filtrate taken up in water (10 mL). This mixture was extracted with ethyl acetate (2×10 mL) and the extracts were dried ($MgSO_4$), before being concentrated in vacuo. The gum remaining was purified by silica chromatography to give the title compound (295 mg, 0.59 mmol) as a gum.

$\delta_H$ (360 MHz, $CDCl_3$): 7.37–7.11 (18H, m), 6.89 (2H, br s), 4.20 (1H, d, J 14.7 Hz), 3.83–3.71 (2H,.m), 3.46–3.37 (3H, m), 3.03 (1H, d, J 14.7 Hz), 2.40–2.35 (3H, m), 2.23–2.14 (3H, m), 1.82–1.78 (1H, m), 1.60–1.50 (2H, m). MS ($ES^+$) 503 (M+H).

DESCRIPTION 23

(1R*,2R*,5S*,6R*)-2-Dibenzylamino-8-benzyl-6-[1-(3-hydroxy)propyloxymethyl]-1-phenyl-8-azabicyclo[3.2.1]octane (1R*,2R*,5S*,6R*)-2-Dibenzylamino-8-benzyl-6-(hydroxymethyl)-1-phenyl-8-azabicyclo[3.2.1]octane (Description 22; 295 mg, 0.59 mmol), 18-crown-6 (396 mg, 1.5 mmol), and 3-(bromopropoxy)-tert-butyldimethylsilane (348 µL, 1.5 mmol) in tetrahydrofuran (5 mL) were treated with 60% sodium hydride suspension in oil (60 mg, 1.5 mmol) and stirred for 16 hours at room temperature. The mixture was poured into saturated aqueous ammonium chloride solution (50 mL) and then extracted with ethyl acetate (2×50 mL). The extracts were dried ($MgSO_4$) and concentrated and the residue dissolved in tetrahydrofuran (10 mL). Tetra-n-butylammonium fluoride solution in tetrahydrofuran (3 mL, 1M, 3 mmol) was then added and the solution stirred for 1 hour at ambient temperature. The solution was poured into water (50 mL) and extracted with ethyl acetate (2×50 mL). The extracts were dried (MgSO$_4$) and concentrated, and the residue purified by silica chromatography to yield the title compound (240 mg, 0.43 mmol).

$\delta_H$ (360 MHz, CDCl): 7.36–7.15 (10H, m), 7.12–7.10 (6H, m), 6.95–6.84 (4H, m), 4.20 (1H, d, J 14.7 Hz), 3.78–3.70 (3H, m), 3.66–3.35 (8H, m), 3.02 (1H, d J 14.7 Hz), 2.47–2.34 (3H, m), 2.26–2.10 (4H, m), 1.85–1.76 (4H, m). MS (ES$^+$) 561 (M+H).

DESCRIPTION 24

(1R*,2R*,5S*,6R*)-2-Amino-6-[1-(3-hydroxy) propyloxymethyl]-1-phenyl-8-azabicyclo[3.2.1] octane (1R*,2R*,5S*,6R*)-2-Dibenzylamino-8-benzyl-6-[1-(3-hydroxy)propyloxymethyl]-1-phenyl-8-azabicyclo[3.2.1] octane (Description 23; 240 mg, 0.43 mmol) and 1,4-cyclohexadiene (812 μL, 8.6 mmol) were dissolved in ethanol (5 mL) and treated with 10% palladium suspended on activated charcoal (100 mg). The resulting suspension was heated at reflux for 16 hours, cooled then filtered. The filtrate was concentrated in vacuo to give the title compound as a gum (71 mg, 0.24 mmol).

$\delta_H$ (360 MHz, CDCl$_3$): 7.34–7.09 (5H, m), 3.79–3.68 (2H, m), 3.64–3.55 (2H, m), 3.52–3.41 (1H, m), 3.38–3.27 (1H, m), 2.50–2.38 (1H, m), 2.33–2.22 (1H, m), 2.20–1.75 (6H, m), 1.66–1.53 (1H, m), 1.51–1.34 (2H, m). MS (ES$^+$) 291 (M+H).

DESCRIPTION 25

2-Bromo-1-chloro-4-(trifluoromethoxy)benzene

To anhydrous copper(II)chloride (6.3 g, 47 mmol) in acetonitrile (100 mL) was added tert-butyl nitrite (6.85 mL, 58 mmol), followed dropwise by a solution of 2-bromo-4-(trifluoromethoxy)aniline (10 g, 39 mmol) in acetonitrile (15 mL). The solution was stirred at ambient temperature for 1 hour then poured into hydrochloric acid (250 mL, 2M). The suspension formed was extracted with diethyl ether (2×250 mL) and the extracts were dried (MgSO$_4$). Concentration yielded the title compound as an oil (7.82 g, 28 mmol).

$\delta_H$ (360 MHz, CDCl$_3$): 7.51 (1H, d, J 3.2 Hz), 7.48 (1H, d, J 8.8 Hz), 7.15 (1H, dd, J 3.2 and 8.8 Hz).

DESCRIPTION 26

1-Chloro-2-vinyl-4-(trifluoromethoxy)benzene

2-Bromo-1-chloro-4-(trifluoromethoxy)benzene (Description 25; 1.0 g, 3.6 mmol) and tri-n-butylvinyl tin (1.21 g, 3.8 mmol) were dissolved in toluene (20 mL) and the solution was degassed for 45 minutes with nitrogen. Tetrakis(triphenylphosphine) palladium (0) (100 mg) was then added and the solution heated at reflux for 2 hours. Once cooled, the solution was concentrated and the residue was purified by silica chromatography to give the title compound (274 mg, 1.2 mmol).

$\delta_H$ (360 MHz, CDCl$_3$): 7.40–7.36 (2H, m), 7.09–7.01 (2H, m), 5.75 (1H, d, J 17.5 Hz), 5.47 (1H, d, J 10.9 Hz).

DESCRIPTION 27

2-Chloro-5-(trifluoromethoxy)benzaldehyde

1-Chloro-2-vinyl-4-(trifluoromethoxy)benzene (Description 26; 274 mg, 1.2 mmol) was dissolved in dichloromethane (15 mL) and methanol (5 mL) and the solution cooled to −78° C. Ozone was then bubbled through until the solution turned blue. Dimethyl sulfide (1 mL) was added and the solution allowed to stir to ambient temperature for 16 hours. Concentration yielded an oil which was purified by silica chromatography to give the title compound (120 mg, 0.53 mmol).

$\delta_H$ (360 MHz, CDCl$_3$): 10.44 (1H, s), 7.77 (1H, d, J 2.3 Hz), 7.51 (1H, d, J 8.7 Hz), 7.39 (1H, dd, J 2.3 and 8.7 Hz).

DESCRIPTION 28

(1R*,2R*,5S*,6R*)-2-Amino-6-(tert-butoxycarbonyl)-1-phenyl-8-azabicyclo[3.2.1]octane (1R*,2R*,5S*,6R*)-2-Benzylamino-8-benzyl-6-(tert-butoxycarbonyl)-1-phenyl-8-azabicyclo[3.2.1]octane (Description 18; 7.07 g, 14.7 mmol) and 10% palladium on activated charcoal (2 g) were taken up in methanol (100 mL) and acetic acid (100 mL), and the mixture was hydrogenated at 50 psi hydrogen for 16 hours at room temperature. The suspension was filtered and the filtrate concentrated in vacuo. The residue was then suspended in saturated aqueous sodium hydrogen carbonate solution (200 mL) and extracted with dichloromethane (2×400 mL). The extracts were dried (MgSO$_4$) and concentrated to give the title compound as a brown oil (4.4 g, 14.6 mmol).

$\delta_H$ (360 MHz, CDCl$_3$): 7.32–7.22 (5H, m), 3.67 (1H, m), 2.84–2.82 (2H, m), 2.54 (1H, dd, J 8.5 and 12.0 Hz), 2.05 (1H, dd, J 4.2 and 12.0 Hz), 1.92–1.83 (2H, m), 1.69 (2H, br s), 1.66–1.62 (1H, m), 1.50–1.44 (1H, m), 1.40 (9H, s). MS (ES$^+$) 303 (M+H).

DESCRIPTION 29

(1R*,5S*,6R*)-8-Benzyl-6-cyano-1-phenyl-8-azabicyclo[3.2.1])oct-3-ene-2-one

N-benzyl-3-hydroxy-2-phenylpyridinium bromide (20 g, 58.3 mmol), acrylonitrile (50 ml, 755 mmol) and triethylamine (20 ml, 143 mmol) were mixed and stirred at reflux for 20 hours in 1,4-dioxane (150 ml). The mixture was partitioned between saturated sodium hydrogen carbonate and ethyl acetate. The organic layer was separated, dried (MgSO$_4$), filtered and concentrated. The residue was chromatographed on silica gel eluting with 25, 35 and 45% diethyl ether/iso-hexanes to yield the title compound (4.4 g, 24%).

$\delta_H$ (400MHz, CDCl$_3$): 7.75–7.73 (2H, m), 7.48–7.28 (8H, m), 6.83 (1H, dd, J 4.8 Hz, 9.7 Hz), 6.24 (1H, d, J 9.7 Hz), 4.12 (1H, m), 3.81 (11H, d, J 14.1 Hz), 3.52 (1H, d, J 14.1 Hz), 3.00 (1H, dd, J 3.5 Hz, 8.3 Hz), 2.80–2.69 (2H, m).

DESCRIPTION 30

(1R*,5S*,6R*)-8-Benzyl-6-cyano-1-phenyl-8-azabicyclo[3.2.1]octan-2-one

Palladium hydroxide (20%) (700 mg) was added to a solution of (1R*,5S*,6R*)-8-benzyl-6-cyano-1-phenyl-8-azabicyclo[3.2.1]oct-3-ene-2-one (Description 29; 7.1 g, 22.6 mmol) in methanol (100 ml). The mixture was transferred to the Parr™ apparatus and hydrogenated at 45 psi for 20 minutes. The mixture was filtered through Celite™ and the filtrate concentrated in vacuo. The residue was partitioned between ethyl acetate and brine. The organic layer was separated, dried (MgSO$_4$), filtered and concentrated to yield the title compound (6.9 g, 96%).

$\delta_H$ (400MHz, CDCl$_3$): 7.75–7.73 (4H, m), 7.51–7.36 (4H, m), 7.32–7.28 (2H, m), 3.86 (1H, s), 3.83 (1H, d, J 14.4 Hz), 3.51 (1H, d, J 14.4 Hz), 3.03 (1H, dd, J 4.7 Hz, 9.5 Hz), 2.91 (1H, dd, J 9.5 Hz,.14.0 Hz), 2.67–2.35 (4H, m), 1.92–1.85 (1H, m).

DESCRIPTION 31

(1R*,2R*,5S*,6R*)-2-Benzylamino-8-benzyl-1-phenyl-6-(1H-tetrazol-5-yl)-8-azabicyclo[3.2.1]octane A mixture of (1R*,5S*,6R*)-8-benzyl-6-cyano-1-phenyl-8-azabicyclo[3.2.1]octan-2-one (Description 30; 2.3 g, 7.3 mmol), p-toluenesulfonic acid monohydrate (5 mg) and benzylamine (1.2 g, 1 mmol) in toluene (10 mL) was heated at reflux under Dean Stark conditions for 24 hours, then cooled and the solvent removed in vacuo. The residue was dissolved in methanol (20 mL) and sodium cyanoborohydride (510 mg, 8 mmol) added. The solution formed was stirred at room temperature for 1 hour then concentrated to approximately ¼ volume. Saturated aqueous sodium hydrogen carbonate solution (50 mL) was added and the suspension formed was extracted with dichloromethane (2×50 mL). The extracts were dried ($MgSO_4$) and concentrated, before the residue was purified by silica chromatography to give the axial and equatorial amines as a mixture (1.47 g, 3.6 mmol). Part of this mixture (1.0 g, 2.5 mmol) was mixed with sodium azide (488 mg, 7.5 mmol) and triethylamine hydrochloride (1.03 mmol) in N-methylpyrrolidinone (5 mL) and heated at 150° C. for 16 hours. After cooling the mixture was diluted with ethyl acetate (50 mL), washed with water (50 mL) and dried ($MgSO_4$). Concentration gave a solid which was purified by silica chromatography to yield the title compound as a tan solid (723 mg, 1.6 mmol).

$\delta_H$ (360 MHz, $CDCl_3$): 7.45–7.13 (15H, m), 4.40 (1H, d, J 13.7 Hz), 3.94 (1H, d, J 13.5 Hz), 3.72 (1H, d, J 13.5 Hz), 3.70 (1H, d, J 13.7 Hz), 3.63 (1H, dd, J 3.9 and 9.3 Hz), 3.47 (1H, s), 3.29 (1H, br s), 2.63 (1H, dd, J 9.3 and 13.7 Hz), 2.47–2.41 (1H, m), 2.12–1.91 (3H, m), 1.38–1.34 (1H, m). MS ($ES^+$) 451 (M+H).

DESCRIPTION 32

(1R*,2R*,5S*,6R*)-2-Amino-1-phenyl-6-(1H-tetrazol-5-yl)-8-azabicyclo[3.2.1]octane (1R*,2R*,5S*,6R*)-2-Benzylamino-8-benzyl-1-phenyl-6-(1H-tetrazol-5-yl)-8-azabicyclo[3.2.1]octane (Description 31; 300 mg, 0.67 mmol) was dissolved in ethanol (10 mL) and treated with 1,4-cyclohexadiene (660 µL, 7 mmol) and 10% palladium on activated charcoal (100 mg). The resulting suspension was heated at reflux for 96 hours, cooled and filtered. The filtrate was concentrated in uacuo to give the title compound as a foam (166 mg, 0.61 mmol).

$\delta_H$ (360 MHz, $CD_3OD$): 7.47–7.29 (5H, m), 3.75–3.71 (2H, m), 3.45 (1H, d, J 3.4 Hz), 3.09 (1H, dd, J 9.0 and 13.6 Hz), 2.39–2.30 (1H, m), 2.13 (1H, dd, J 4.8 and 13.6 Hz), 1.99–1.84 (2H, m), 1.77–1.69 (1H, m). MS ($ES^+$) 271 (M+H).

DESCRIPTIONS 33a and 33b (a) (1R*,2R*,5S*,6R*)-2-Benzylamino-8-benzyl-1-phenyl-6-(1-methyl-1H-tetrazol-5-yl)-8-azabicyclo[3.2.1]octane; and (b) (1 R*,2R*,5S*,6R*-2-Benzylamino-8-benzyl-1-phenyl-6-(2-methyl-2H-tetrazol-5-yl)-8-azabicyclo[3.2.1]octane (1R*,2R*,5S*,6R*)-2-Benzylamino-8-benzyl-1-phenyl-6-(1H-tetrazol-5-yl)-8-azabicyclo[3.2.1]octane (Description 31; 370 mg, 0.82 mmol) was dissolved in a mixture of toluene (5 mL) and methanol (5mL), and treated with a solution of (trimethylsilyl)diazomethane in hexane (700 µL, 2M, 1.4 mmol). After stirring at room temperature for 15 minutes, the solution was concentrated in vacuo and the residue purified by silica chromatography, to give the two title compounds.

Description 33a (57 mg, 0.12 mmol) (most polar): $\delta_H$ (400 MHz, $CDCl_3$): 7.53–7.52 (2H, m), 7.36–7.21 (13H, m), 4.37 (1H, d, J 15.0 Hz), 3.92 (1H, d, J 13.5 Hz), 3.86 (3H, s), 3.74–3.70 (2H, m), 3.47 (1H, br s), 3.37 (1H, dd, J 4.8 and 6.4 Hz), 3.27 (1H, d, J 3.8 Hz), 2.86–2.76 (1H, m), 2.54 (1H, dd, J 6.4 and 12.0 Hz), 2.48–2.37 (1H, m), 2.14 (1H, dd, J 4.8 and 12.0 Hz), 2.03–1.95 (1H, m), 1.29–1.24 (1H, m). MS ($ES^+$) 465 (M+H).

Description 33b (357 mg, 0.77 mmol) (least polar): $\delta_H$ (400 MHz, $CDCl_3$): 7.51–7.49 (2H, m), 7.32–7.13 (13H, m), 4.36 (1H, d, J 15.3 Hz), 4.31 (3H, s), 3.92 (1H, d, J 13.6 Hz), 3.71–3.65 (3H, m), 3.52 (1H, dd, J 6.2 and 8.2 Hz), 3.22 (1H, d, J 2.8 Hz), 2.57–2.55 (2H, m), 2.33–2.31 (1H, m), 2.09–1.98 (2H, m), 1.35–1.32 (1H, m). MS ($ES^+$) 465 (M+H).

DESCRIPTION 34

(1R*,2R*,5S*,6R*)-2-Amino-1-phenyl-6-(1-methyl-1H-tetrazol-5-yl)-8-azabicyclo[3.2.1]octane (1R*,2R*,5S*,6R*)-2-Benzylamino-8-benzyl-1-phenyl-6-(1-methyl-1H-tetrazol-5-yl)-8-azabicyclo[3.2.1]octane (Description 33a; 57 mg, 0.12 mmol) was dissolved in ethanol (5 mL) and treated with 1,4-cyclohexadiene (5 mL), followed by 10% palladium on activated charcoal (50 mg). The suspension formed was heated at reflux for 72 hours, then cooled and filtered. The filtrate was concentrated, and the residue taken up in ethyl acetate (2 mL) and treated with ethereal hydrogen chloride (2 mL, 1M). The solid formed was removed by filtration, washed with diethyl ether and dried to give the crude title compound as a solid (27 mg). MS ($ES^+$) 285 (M+H).

DESCRIPTION 35

(1R*,2R*,5S*,6R*)-2-Amino-1-phenyl-6-(2-methyl-2H-tetrazol-5-yl)-8-azabicyclo[3.2.1]octane (1R*,2R*,5S*,6R*)-2-Benzylamino-8-benzyl-1-phenyl-6-(2-methyl-2H-tetrazol-5-yl)-8-azabicyclo[3.2.1]octane (Description 33b; 357 mg, 0.77 mmol) was dissolved in ethanol (10 mL) and treated with 1,4-cyclohexadiene (5 mL), followed by 10% palladium on activated charcoal (300 mg). The suspension formed was heated at reflux for 72 hours, then cooled and filtered. The filtrate was concentrate to give the title compound as a gum (239 mg, 0.67 mmol).

$\delta_H$ (400 MHz, $CD_3OD$): 7.57–7.47 (5H, m), 4.29 (3H, s), 4.07–4.00 (1H, m), 3.92–3.87 (1H, m), 3.54–3.40 (1H, m), 2.82–2.70 (1H, m), 2.68–2.51 (2H, 2.22–1.98 (3H, m). MS ($ES^+$) 285 (M+H).

DESCRIPTIONS 36a, 36b AND 36c (a) (1R*,3S*,5S*,6R*)-8-Benzyl-3-fluoro-1-phenyl-6-(tert-butoxycarbonyl)-8-azabicyclo[3.2.1]octan-2-one;

(b) (1R*,3R*,5S*,6R*)-8-Benzyl-3-fluoro-1-phenyl-6-(tert-butoxycarbonyl)-8-azabicyclo[3.2.1]octan-2-one; and (c) (1R*,5S*,6R*)-8-Benzyl-3,3-difluoro-1-phenyl-6-(tert-butoxycarbonyl)-8-azabicyc,lo[3.2.1]octan-2-one To a solution of lithium hexamethyldisilazide in tetrahydrofuran (18 mL, 1M, 18 mmol) was added tetrahydrofuran (100 mL), and the mixture cooled to −78° C. A solution of (1R*,5S*,6R*)-8-benzyl-1-phenyl6-(tert-butoxycarbonyl)-8-azabicyclo[3.2.1]octan-2-one (Description 17; 5.0 g, 12.8 mmol) was then slowly added. The temperature was allowed to warm to −50° C., then was immediately stirred back to −78° C. for 30 minutes. N-Fluorobenzenesulfonimide (5.7 g, 18 mmol) dissolved in tetrahydrofuran (50 mL) was then added, and the solution was allowed to stir to −30° C. for 30 minutes. Saturated aqueous ammonium chloride solution (100 mL) was added, and the mixture was extracted with ethyl acetate (2×200 mL). After drying (MgSO$_4$), the extracts were concentrated and the residue purified by silica chromatography to give the three products:

Description 36a (1.62 g, 4.0 mmol) (most polar): $\delta_H$ (400 MHz, CDCl$_3$): 7.52–7.49 (2H, m), 7.42–7.25 (8H, m), 5.36 (1H, dt, 9.1 and 49.7 Hz), 3.82 (1H, d, J 14.6 Hz), 3.83–3.78 (1H, m), 3.31 (1H, d, J 14.6 Hz), 2.91 (1H, dd, J 3.9 and 9.4 Hz), 2.73–2.63 (3H, m), 2.50 (1H, dd, J 9.4 and 14.9 Hz), 1.45 (9H, s). MS (ES$^+$) 410 (M+H).

Description 36b (1.67 g, 4.1 mmol): $\delta_H$ (400 MHz, CDCl$_3$): 7.46–7.23 (10, m), 5.68 (1H, ddd, J 6.0, 10.8 and 50.7 Hz), 3.77–3.72 (1H, m), 3.46 (1H, d, J 13.7 Hz), 3.26 (1H, d, J 13.7 Hz), 3.06–2.95 (1H, m), 2.83–2.72 (3H, m), 1.71–1.60 (1H, m), 1.46 (9H, s). MS (ES$^+$) 410 (M+H).

Description 36c (1.76 g, 4.1 mmol) (least polar): $\delta_H$ (400 MHz, CDCl$_3$): 7.52–7.50 (2H, m), 7.29–7.40 (8H, m), 3.83 (1H, t, J 4.3 Hz), 3.76 (1H, d, J 14.9 Hz), 3.35 (1H, d, J 14.9 Hz), 3.08 (1H, dd, J 5.1 and 9.4 Hz), 2.93–2.70 (3H, m), 2.62–2.50 (1H, m), 1.45 (9 H, s). MS (ES$^+$) 428 (M+H).

DESCRIPTION 37

(1R*,2R*,3S*,5S*,6R*)-2-Benzylamino-8-benzyl-3-fluoro-1-phenyl-6-(tert-butoxycarbonyl)-8-azabicyclo[3.2.1]octane (1R*,3S*,5S*,6R*)-8-Benzyl-3-fluoro-1-phenyl-6-(tert-butoxycarbonyl)-8-azabicyclo[3.2.1]octan-2-one (Description 36a; 1.68 g, 4.1 mmol), titanium iso-propoxide (1.8 mL, 6.2 mmol) and benzylamine (520 μL, 4.7 mmol) were heated together at 85° C. for two hours, then cooled and diluted with methanol (30 mL). The solution was then heated to 50° C. and sodium borohydride (1.06 g, 28 mmol) was added portionwise over 4 hours. After addition was complete, the solution was heated for a further 16 hours, then cooled and poured into aqueous sodium hydroxide solution (100 mL, 1M). The suspension formed was extracted with ethyl acetate (2×100 mL) and the extracts were dried (MgSO$_4$). Concentration in vacuo gave a gum which was purified by silica chromatography to give the title compound (651 mg, 1.3 mmol).

$\delta_H$ (360 MHz, CDCl$_3$): 7.50–7.48 (2H, m), 7.39–7.18 (13H, m), 5.05 (1H, dm, J 47.3 Hz), 4.13 (1H, d, J 15.1 Hz), 4.04 (1H, d, J 13.3 Hz), 3.74–3.72 (3H, m), 3.62 (1H, d, J 15.1 Hz), 2.61 (1H, dd, J 4.6 and 9.1 Hz), 2.48–2.36 (2H, m), 2.02 (1H, dd, J 9.1 and 13.7 Hz), 1.87–1.82 (1H, m), 1.39 (9H, s). MS (ES$^+$) 501 (M+H).

DESCRIPTION 38

(1R*,2R*,3S*,5S*,6R*)-2-Benzylamino-8-benzyl-3-fluoro-1-phenyl-6-(hydroxymethyl)-8-azabicyclo[3.2.1]octane (1R*,2R*,3S*,5S*,6R*)-2-Benzylamino-8-benzyl-3-fluoro-1-phenyl-6-(tert-butoxycarbonyl)-8-azabicyclo[3.2.1]octane (Description 36b; 651 mg, 1.3 mmol) was dissolved in tetrahydrofuran (10 mL) and then treated with a solution of lithium triethylborohydride in tetrahydrofuran (4 mL, 1M, 4 mmol). The solution was stirred at room temperature for 1 hour, then poured into aqueous sodium hydroxide solution (50 mL, 1M). The suspension formed was extracted with ethyl acetate (2×100 mL) and the extracts were dried (MgSO$_4$). Concentration in vacuo gave a gum which was purified by silica chromatography to give the title compound (476 mg, 1.1 mmol).

$\delta_H$ (400 MHz, CDCl$_3$): 7.51–7.49 (2H, m), 7.41–7.20 (13H, m), 5.15 (1H, dm, J 47.3 Hz), 4.22 (1H, d, J 14.1 Hz), 4.13 (1H, d, J 12.9 Hz), 3.93 (1H, t, J 4.3 Hz), 3.81–3.77 (2H, m), 3.57–3.49 (1H, m), 3.37–3.34 (1H, m), 2.55 (1H, dq, J 2.7 and 12.1 Hz), 2.08–1.98 (2H, m), 1.78–1.72 (1H, m), 1.60–1.56 (1H, m). MS (ES$^+$) 431 (M+H).

DESCRIPTION 39

(1R*,2R*,3S*,5S*,6R*)-2-Amino-3-fluoro-1-phenyl-6-(hydroxymethyl)-8-azabicyclo[3.2.1]octane (1R*,2R*,3S*,5S*,6R*)-2-Benzylamino-8-benzyl-3-fluoro-1-phenyl-6-(hydroxymethyl)-8-azabicyclo[3.2.1]octane (Description 38; 486 mg, 1.13 mmol) was dissolved in ethanol (20 mL) and 1,4-cyclohexadiene (2 mL). 10% Palladium on activated charcoal (500 mg) was added and the suspension was heated at reflux for 24 hours. After cooling and filtration, the filtrate was concentrated in vacuo to give the title compound as a gum (257 mg, 1.0 mmol).

$\delta_H$ (360 MHz, CD$_3$OD): 7.36–7.24 (5H, m), 5.05 (1H, dm, J 47.1 Hz), 3.55–3.48 (1H, m), 3.40 (1H, d, J 6.8 Hz), 2.48 (1H, dd, J 8.7 and 13.7 Hz), 2.21–2.13 (1H, m), 2.01–1.87 (2H, m), 1.40 (1H, dd, J 4.5 and 13.7 Hz). MS (ES$^+$) 251 (M+H).

EXAMPLE 1

(1R*,2R*,5S*)-2-(3,5-bis(Trifluoromethyl)benzylamino)-1-phenyl-8-azabicyclo[3.2.1]octane Dihydrochloride (1R*,2R*,5S*)-2-Amino-1-phenyl-8-azabicyclo[3.2.1]octane (Description 6; 97 mg, 0.48 mmol) and 3,5-bis(trifluoromethyl)benzaldehyde (121 mg, 0.5 mmol) were dissolved in 1,2-dichloroethane (10 mL) and treated with acetic acid (30 μL). The solution was stirred at room temperature for 16 hours then concentrated. The residue was taken up in methanol (10 mL) and treated with sodium cyanoborohydride (60 mg), then heated at 80° C. for 2 hours, concentrated in vacuo and the residue suspended in saturated sodium bicarbonate solution (10 mL). This was extracted with dichloromethane (2×10 mL) and the extracts dried (MgSO$_4$), then concentrated. The residue was taken up in ethyl acetate (10 mL) and treated with ethereal hydrogen chloride (1M, 2 mL). The suspension formed was concentrated in vacuo and the solid remaining recrystallized from methanol/diethyl ether, to give the title compound as a white solid (167 mg, 0.33 mmol).

$\delta_H$ (360 MHz, D$_6$-DMSO, 340K): 7.88 (1H, s), 7.78 (2H, s), 7.43–7.39 (5H, m), 4.11 (1H, br d, J 6.7 Hz), 3.70 (1H, d, J 14.3 Hz), 3.28–3.24 (2H, m), 2.78–2.67 (1H, m), 2.30–1.91 (6H, m), 1.63 (1H, br d, J 13.1 Hz). MS (ES$^+$) 429 (M+H).

EXAMPLE 2

(1R*,2R*,5S*)-2-(2-Methoxy-5-(trifluoromethoxy)benzylamino)-1-phenyl-8-azabicyclo[3.2.1]octane Dihydrochloride Prepared according to the method of Example 1 from the product of Description 6 and 2-methoxy-5-

(trifluoromethoxy)benzylaldehyde. H (360 MHz, D₆-DMSO, 340K): 7.48–7.39 (5H, m), 7.23–7.21 (2H, m), 6.97–6.94 (1H, m), 4.14–4.12 (1H, m), 3.69 (1H, d, J 14.1 Hz), 3.60 (3H, s), 3.42–3.34 (2H, m), 2.79–2.71 (1H, m), 2.29–1.92 (6H, m), 1.66–1.62 (1H, m). MS (ES⁺) 407 (M+H).

EXAMPLE 3

(1R*,2R*,5S*)-2-(2-Cyclopropyloxy-5-[5-(trifluoromethyl)tetrazol-1-yl]benzylamino)-1-phenyl-8-azabicyclo[3.2.1]octane (1R*,2R*,5S*)-2-Amino-1-phenyl-8-azabicyclo[3.2.1]octane (Description 6; 50 mg, 0.25 mmol) and 2-(cyclopropoxy)-5-[5-(trifluoromethyl)tetrazol-1-yl]benzaldehyde (119 mg, 0.4 mmol) [See International (PCT) Patent Publication No. WO 99/24423, published 20 May 1999] were dissolved in 1,2-dichloroethane (5 mL) and treated with acetic acid (23 μL), followed by sodium triacetoxyborohydride (85 mg). The solution was stirred at ambient temperature for 16 hours, then quenched with saturated aqueous sodium hydrogen carbonate solution (50 mL). The mixture was extracted with dichloromethane (2×50 mL) and the extracts were dried (MgSO₄), then concentrated. The residue was purified by silica chromatography to give the free base, which was taken up in ethyl acetate (10 mL) and treated with ethereal hydrogen chloride (1M, 2 mL). The solid formed was removed by filtration and recrystallized from methanol/ethyl acetate to give the title compound as a white solid (84 mg, 0.15 mmol).

$\delta_H$ (360 MHz, CD₃OD): 7.67–7.64 (1H, m), 7.57–7.50 (7H, m), 4.35–4.33 (1H m), 4.15 (1H, br d, J 13.4 Hz), 3.88–3.86 (2H, m), 3.65 (1H, br d, J 13.4 Hz), 2.95–2.87 (1H, m), 2.61–2.54 (1H, m), 2.42–2.13 (5H, m), 1.90–1.86 (1H, m), 0.88–0.82 (4H, m), 0.77–0.69 (1H, m). MS (ES⁺) 485 (M+H).

EXAMPLE 4

(1R*,2R*,5S*)-2-(2-Methoxy-5-(trifluoromethoxy)benzylamino)-8-benzyl-1-phenyl-8-azabicyclo[3.2.1]octane Dihydrochloride (1R*,2R*,5S*)-2-amino-8-benzyl-1-phenyl-8-azabicyclo[3.2.1]octane (Description 9; 156 mg, 0.53 mmol) and 2-methoxy-5-(trifluoromethoxy)benzaldehyde (132 mg, 0.6 mmol) were dissolved in 1,2-dichloroethane (10 mL) and acetic acid (35 μL), and treated with sodium triacetoxyborohydride (127 mg, 0.6 mmol). The suspension formed was stirred at ambient temperature for 16 hours, then quenched with saturated aqueous sodium hydrogen carbonate solution (50mL). The mixture was extracted with dichloromethane (2×50 mL) and the extracts were dried (MgSO₄), then concentrated. Purification of the residue gave the desired free base which was taken up in ethyl acetate (10 mL) and treated with ethereal hydrogen chloride (1M, 2 mL). The solid formed was recovered by filtration and recrystallized from methanol/diethyl ether to give the title compound as a white solid (178 mg, 0.3 mmol).

$\delta_H$ (360 MHz, CD₃OD, 330K): 7.81(2H, br s), 7.69–7.58 (5H, m), 7.46–7.44 (3H, m), 7.30 (1H, br d, J 9.0 Hz), 7.24 (1H, br s), 7.01 (1H, d, J 9.0 Hz), 4.28 (1H, br d, J 13.5 Hz), 3.92–3.88 (2H, m), 3.63–3.61 (1H, m), 3.61 (3H, s), 3.47–3.46 (1H, m), 2.95–2.86 (2H, m), 2.56–2.12 (6H, m), 1.83–1.79 (1H, m). MS (ES⁺) 497 (M+H).

EXAMPLE 5

(1R*,2R*,5S*)-2-(2-Cyclopropoxy-5-(trifluoromethoxy)-benzylamino)-1-phenyl-8-azabicyclo[3.2.1]octane Dihydrochloride (1R*,2R*,5S*)-2-Amino-1-phenyl-8-azabicyclo[3.2.1]loctane (Description 6; 116 mg, 0.57 mmol) and 2-(cyclopropoxy)-5-(trifluoromethoxy)benzaldehyde (Description 13; 100 mg, 0.41 mmol) were dissolved in 1,2-dichloroethane (5 mL) and acetic acid (1mL), then treated with sodium triacetoxyborohydride (318 mg, 1.5 mmol). The suspension formed was stirred at room temperature for 4 hours, then quenched with saturated aqueous sodium hydrogen carbonate solution (25 mL). The suspension formed was extracted with dichloromethane (2×25 mL) and the extracts dried (MgSO₄), then concentrated. Purification of the residue by silica chromatography yielded the free base as a gum. This was taken up in ethyl acetate (10 mL) and treated with ethereal hydrogen chloride (1M, 2 mL). The solid formed was recovered by filtration and washed with ethyl acetate. Drying in vacuo yielded the title compound as a white powder (130 mg, 0.26 mmol).

$\delta_H$ (360 MHz, CD₃OD): 7.58–7.49 (5H, m), 7.35–7.29 (2H, m), 7.23 (1H, s), 4.36–4.34 (1H, m), 4.12 (1H, br d, J 13.3 Hz), 3.83 (1H, br s), 3.77–3.71 (1H, m), 3.69 (1H, br d, J 13.3 Hz), 2.96–2.87 (1H, m), 2.65–2.57 (1H, m), 2.49–2.12 (5H, m), 1.92–1.86 (1H, m), 0.82–0.75 (3H, m), 0.65–0.60 (1H, m). MS (ES⁺) 433 (M+H).

EXAMPLE 6

(1R*,2R*,5S*,6R*)-2-(2-Methoxy-5-(trifluoromethoxy)benzylamino)-1-phenyl-6-phenylsulphonyl-8-azabicyclo[3.2.1]octane Dihydrochloride (1R*,2R*,5S*,6R*)-2-amino-1-phenyl-6-phenylsulphonyl-8-azabicyclo[3.2.1]octane (Description 6; 90 mg, 0.26 mmol) and 2-methoxy-5-(trifluoromethoxy)benzaldehyde (116 mg, 0.54 mmol) were dissolved in 1,2-dichloromethane (5 mL) and acetic acid (35 μL), and treated with sodium triacetoxyborohydride (165 mg, 0.78 mmol). The suspension was stirred at room temperature for 16 hours, then at 60° C. for 2 hours. After cooling the mixture was poured into saturated aqueous sodium hydrogen carbonate solution (20 mL) and extracted with dichloromethane (2×25 mL). The extracts were dried (MgSO₄) and concentrated. Purification of the residue by silica chromatography yielded the free base as a gum. This was taken up in ethyl acetate (10 mL) and treated with ethereal hydrogen chloride (1M, 2 mL). The solid formed was recovered by filtration and recrystallized form methanol/diethyl ether to yield the title compound as a white powder (109 mg, 0.18 mmol).

$\delta_H$ (360 MHz, CD₃OD): 7.90–7.88 (2H, m), 7.77–7.72 (1H, m), 7.65–7.61 (2H, m), 7.47–7.45 (3H, m), 7.35–7.29 (3H, m), 7.15 (1H, br s), 7.00–7.98 (1H, m), 4.11–4.12 (1H, m), 4.06–4.01 (2H, m), 3.83–3.79 (1H, m), 3.58 (3H, s), 3.37–3.38 (1H, m), 2.88–2.82 (1H, m), 2.14–1.95 (4H, m), 1.56–1.53 (1H, m). MS (ES⁺) 547 (M+H).

EXAMPLE 7

(1R*,2R*,5S*,9S*)- and (1R*,2R*,5S*, 9R*)-2-[1-(2-Methoxy-5-(trifluoromethoxy)phenyl)ethylamino]-1-phenyl-8-azabicyclo[3.2.1]octane Dihydrochlorides (1R*,2R*,5S*,6R*)-2-Amino-1-phenyl-8-azabicyclo[3.2.1]octane (Description 6; 78 mg, 0.39, mmol) and 2-methoxy-5-(triflouromethoxy)acetophenone (116 mg, 0.54 mmol) were dissolved in 1,2-dichloromethane (5 mL) and acetic acid (35 μL), and treated with sodium triacetoxyborohydride (170 mg, 0.8 mmol). The suspension was stirred at room temperature for 16 hours, then at 100° C. for 4 hours. After cooling the mixture was poured into saturated aqueous sodium hydrogen carbonate solution (20 mL) and extracted with dichloromethane (2×25 mL). The extracts were dried (MgSO₄) and concentrated. Purification of the residue by silica chromatography yielded the free bases as a gum. The diastereomers were then separated by chiral preparative HPLC. Each of the free bases were then taken up in ethyl acetate (10 mL) and treated with ethereal hydrogen chloride (1M, 2 mL). The solid formed was recovered by filtration and washed with ethyl acetate to yield the two dihydrochloride salts (16 mg and 4 mg).

Diastereomer A (Most polar):

$\delta_H$ (360 MHz, CD₃OD): 7.57–7.46 (5H, m), 7.24 (1H, br d, J 8.9 Hz), 7.04 (1 h, d, J 8.9 Hz), 6.76 (1H, br s), 4.27–4.29 (1H, m), 3.78 (3H, s), 3.49–3.40 (2H, m), 2.87–2.80 (1H, m), 2.44–2.24 (3H, m), 2.16–1.81 (4H, m), 1.29–1.2 (3H, m). MS (ES⁺) 421 (M+H).

Diastereomer B (Least Polar):

$\delta_H$ (400 MHz, CD₃OD): 7.55–7.52 (3H, m), 7.30–7.28 (2H, m), 7.15 (1H, br d, J 8.9 Hz), 6.91–6.88 (2H, m), 4.19–4.15 (1H, m), 3.38 (3H, s), 2.79–2.76, (1H, m), 2.37–1.94 (5H, m), 1.73–1.69 (1H, m), 1.33–1.26 (3H, m). MS (ES⁺) 421 (M+H).

EXAMPLE 8

(1R*,2R*,5S*,6R*)-2-(2-Cyclopropoxy-5-(trifluoromethoxy)-benzylamino)-6-(hydroxymethyl)-1-phenyl-8-azabicyclo[3.2.1]octane Dihydrochloride Prepared according to the method of Example 5 from the product of Description 20 and Description 13.

$\delta_H$ (360 MHz, CD₃OD): 7.56–7.48 (5H, m), 7.33–7.26 (2H, m), 7.19–7.18 (1H, m), 4.23–4.21 (1H, m), 4.06–4.01 (1H, m), 3.70–3.60 (4H, m), 3.50 (1H, dd, J 6.4 and 10.5 Hz), 3.04 (1H, dd, J 9.5 and 14.4 Hz), 2.65–2.55 (2H, m), 2.37–2.31 (2H, m), 2.01–1.87 (2H, m), 0.80–0.55 (4H, m). MS (ES⁺) 464 (M+2H).

EXAMPLE 9

(1R*,2R*,5S*)-2-(2-Chloro-5-(trifluoromethoxy)benzylamino)-1-phenyl-8-azabicyclo[3.2.1]octane Dihydrochloride (1R*,2R*,5S*)-2-Amino-1-phenyl-8-azabicyclo[3.2.1]octane (Description 6; 77 mg, 0.38 mmol) and 2-chloro-5-(trifluoromethoxy)benzaldehyde (Description 27; 120 mg, 0.53 mmol) were dissolved in 1,2-dichloroethane (5 mL) and acetic acid (1mL), then treated with sodium triacetoxyborohydride (128 mg, 0.6 mmol). The suspension was stirred at room temperature for 16 hours, then diluted with methanol (5 mL). Sodium cyanoborohydride was added (200 mg, 0.9 mmol) and this solution stirred for a further 16 hours at ambient temperature. The resulting mixture was poured into saturated aqueous sodium hydrogen carbonate solution (50 mL) and extracted with dichloromethane (2×50 mL). The extracts were dried (MgSO₄) and concentrated to yield a gum, which was purified by silica chromatography. The pure free base was dissolved in ethyl acetate (10 mL) and treated with ethereal hydrogen chloride (2 mL, 1M). The solid formed was removed by filtration, washed with diethyl ether and dried to give the title compound as a solid (46 mg, 0.1 mmol).

$\delta_H$ (360 MHz, CD₃OD): 7.53–7.40 (7H, m), 7.27–7.25 (1H, m), 4.30 (1H, d, J 6.7 Hz), 3.96 (1H, d, J 14.0 Hz), 3.65 (1H, br s), 3.48 (1H, d, J 14.0 Hz), 2.92–2.84 (1H, m), 2.48–2.11 (6H, m), 1.85–1.80 (1H, m). MS (ES⁺) 412 (M+H).

EXAMPLE 10

(1R*,2R*,5S*,6R*)-2-(2-Cyclopropoxy-5-(trifluoromethoxy)-benzylamino)-6-[1-(3-hydroxy)propyloxymethyl]-1-phenyl-8-azabicyclo[3.2.1]octane Dihydrochloride Prepared according to the method of Example 6 from the product of Description 24 and 2-cyclopropoxy-5-(trifluoromethoxy)benzaldehyde.

$\delta_H$ (360 MHz, CDCl₃): 7.65–7.50 (2H, m), 7.48–7.39 (3H, m), 7.29–7.26 (1H, m), 7.15–7.06 (2H, m), 4.41 (1H, br s), 4.24–4.20 (1H, m), 4.01 (1H, d, J 13.1 Hz), 3.89–3.52 (7H, m), 3.17–3.14 (1H, m), 2.83–2.38 (5H, m), 2.12–2.07 (1H, m), 2.01–1.95 (1H, m), 1.73–1.64 (2H, m), 0.71 (4H, d, J 5.3 Hz). MS (ES⁺) 521 (M+H).

EXAMPLE 11

(1R*,2R*,5S*,6R*)-2-(2-Cyclopropoxy-5-(trifluoromethoxy)-benzylamnino)-6-(tert-butoxycarbonyl)-1-phenyl-8-azabicyclo[3.2.1]octane Prepared according to the method of Example 1 from the product of Description 28 and 2-cyclopropoxy-5-(trifluoromethoxy)benzaldehyde.

$\delta_H$ (360 MHz, CDCl₃): 7.26–7.20 (5H, m), 6.99–6.97 (2H, m), 6.73 (1H, br s), 3.72 (1H, m), 3.52 (1H, d, J 14.8 Hz), 3.43 (1H, m), 3.30 (1H, d, J 14.8 Hz), 2.79 (1H, dd, J 4.6 and 9.2 Hz), 2.59 (1H, d, J 2.9 Hz), 2.41 (1H, dd, J 9.2 and 13.3 Hz), 1.96 (1H, dd, J 4.6 Hz and 13.3 Hz), 1.86–1.78 (1H, m), 1.70–1.55 (3H, m), 1.39 (9H, s), 0.66–0.64 (2H, m), 0.53–0.51 (2H, m). MS (ES⁺) 533 (M+H).

EXAMPLE 12

(1R*,2R*,5S*,6R*)-2-(2-Cyclopropoxy-5-(trifluoromethoxy)-benzylamino)-6-(N-methoxy-N-methylcarboxamido)-1-phenyl-8-azabicyclo[3.2.1]octane (1R*,2R*,5S*,6R*)-2-(2-Cyclopropoxy-5-(trifluoromethoxy)benzylamino)-6-(tert-butoxycarbonyl)-1-phenyl-8-azabicyclo[3.2.1]octane (Example 11; 294 mg, 0.55 mmol) was taken up in 30% trifluoroacetic acid in dichloromethane (10 mL) and stirred at room temperature for 4 hours. After concentration in vacuo, the residue was dissolved in dichloromethane (15 mL), and treated with triethylamine (612 µL, 4.4 mmol), N,O-dimethylhydroxylamine hydrochloride (107 mg, 1.1 mmol), N,N-dimethylaminopyridine (10 mg) and 1-(3-dimethylaminopropyl)-3-ethylcarbodiimide hydrochloride (115 mg, 0.6 mmol). The solution formed was stirred at room temperature for 4 hours, then poured into water (50 mL). Extraction with dichloromethane (2×50 mL) and concentration of the dried (MgSO₄) extracts gave the crude product as a gum. Purification by silica chromatography yielded the title compound (160 mg, 0.31 mmol).

$\delta_H$ (360 MHz, CDCl₃): 7.26–7.17 (5H, m), 7.00–6.97 (2H, m), 6.74 (1H, br s), 3.70 (3H, s), 3.53 (1H, d, J 14.8 Hz), 3.45–3.28 (3H, m), 3.14 (3H, s), 2.63 (1H, m), 2.43–2.35 (2H, m), 2.08–1.97 (3H, m), 1.88–1.84 (1H, m), 1.44–1.41 (1H, m), 0.67–0.63 (2H, m), 0.54–0.51 (2H, m). MS (ES⁺) 520 (M+H).

EXAMPLE 13

(1R*,2R*,5S*,6R*)-2-(2-Cyclopropoxy-5-(trifluoromethoxy)-benzylamino)-6-acetyl-1-phenyl-8-azabicyclo[3.2.1]octane (1R*,2R*,5S*,6R*)-2-(2-Cyclopropoxy-5-(trifluoromethoxy)benzylamino)-6-(N-methoxy-N- methylcarboxamido)-1-phenyl-8-azabicyclo[3.2.1]octane (Example 12; 490 mg, 0.95 mmol) was dissolved in tetrahydrofuran (10 mL) and cooled to 0° C. A solution of methylmagnesium chloride in tetrahydrofuran (1mL, 3M, 3 mmol) was then added and the solution was stirred at 0° C. for 1 hour and then allowed to stir to room temperature over 2 hours. The solution was poured into saturated aqueous ammonium chloride solution (20 mL), extracted with ethyl acetate (2×20 mL) and the extracts were dried (MgSO$_4$). Concentration in vacuo gave an oil which was purified by silica chromatography to give the title compound as a tan oil (356 mg, 0.75 mmol).

$\delta_H$ (400 MHz, CDCl$_3$): 7.28–7.19 (5H, m), 7.01–6.98 (2H, m), 6.76 (1H, br s), 3.70 (1H, t, J 2.6 Hz), 3.54 (1H, d, J 14.7 Hz), 3.43 (1H, m), 3.33 (1H, d, J 14.7 Hz), 3.00 (1H, dd, J 4.8 and 9.0 Hz), 2.63 (1H, d, J 2.6 Hz), 2.28 (1H, dd, J 9.0 and 13.2 Hz), 2.18 (3H, s), 2.04–1.94 (2H, m), 1.90–1.84 (1H, m), 1.73–1.71 (1H, m), 1.45–1.42 (1H, m), 0.67–0.63 (2H, m), 0.52–0.48 (2H, m). MS (ES$^+$) 475 (M+H).

EXAMPLE 14

(1R*,2R*,5S*,6R*,R*) and (1R*,2R*,5S*,6R*,S*)-2-(2-Cyclopropoxy5-(trifluoromethoxy)benzylamino)-6-(l-hydroxy)ethyl-1-phenyl-8-azabicyclo[3.2.1]octane Dihydrochlorides (1R*,2R*,5S*,6R*)-2-(2-Cyclopropoxy-5-(trifluoromethoxy)benzylamino)-6-acetyl-1-phenyl-8-azabicyclo[3.2.1]octane (Example 13; 109 mg, 0.23 mmol) in methanol (5 mL was treated with sodium borohydride (8.7 mg, 0.23 mmol) and the solution was stirred for 15 minutes, before being poured into saturated aqueous sodium hydrogen carbonate solution (20 mL). The solution was extracted with dichloromethane (2×20 mL), and the extracts were dried (MgSO$_4$) then concentrated. The residue was purified by silica chromatography to give the two diastereomers. Each one was taken up in ethyl acetate (5 mL) and treated with ethereal hydrogen chloride (1mL, 1M). The solid formed was removed by filtration, washed with diethyl ether and dried to give the title compounds as solids (16 mg of each).

Least Polar Compound:

$\delta_H$ (400 MHz, CD$_3$OD): 7.56–7.49 (5H, m), 7.33–7.27 (2H, m), 7.18 (1H, br s), 4.01–3.94 (1H, m), 3.69–3.62 (3H, m), 2.86 (1H, dd, J 9.2 and 14.1 Hz), 2.59–2.55 (1H, m), 2.43–2.23 (4H, m), 2.03–1.89 (3H, m), 1.12 (3H, d, J 6.3 Hz), 0.78–0.68 (3H, m), 0.58–0.55 (1H, m). MS (ES$^+$) 477 (M+H).

Most Polar Compound:

$\delta_H$ (400 MHz, CD$_3$OD): 7.54–7.42 (5H, m), 7.30–7.23 (2H, m), 7.13 (1H, br s), 3.97–3.93 (1H, m), 3.66–3.54 (4H, m), 3.03 (1H, dd, J 9.72 and 14.1 Hz), 2.54–2.50 (1H, m), 2.33–2.24 (3H, m), 2.03–2.00 (1H, m), 1.91 (1H, dd, J 4.4 and 14.1 Hz), 1.82–1.79 (1H, m), 1.20 (3H, d, J 6.2 Hz), 0.80–0.53 (4H, m). MS (ES$^+$) 477 (M+H).

EXAMPLE 15

(1R*,2R*,5S*,6R*)-2-(2-Cyclopropoxy-5-(trifluoromethoxy)-benzylamino)-6-(1-hydroxy-1-methyl)ethyl-1-phenyl-8-azabicyclo[3.2.1]octane Dihydrochloride (1R*,2R*,5S*,6R*)-2-(2-Cyclopropoxy-5-(trifluoromethoxy)benzylamino)-6-acetyl-1-phenyl-8-azabicyclo[3.2.1]octane (Example 13; 132 mg, 0.28 mmol) in tetrahydrofuran (2 mL) was cooled to −70° C. and a solution of methylmagnesium chloride in tetrahydrofuran (300 μL, 3M, 0.9 mmol) was slowly added. After addition was complete, the solution was allowed to stir to room temperature over 1 hour, and was then poured into saturated aqueous ammonium chloride solution (10 mL). Extracted with ethyl acetate (2×10 mL) and the extracts were dried (MgSO$_4$). Concentration in vacuo gave a gum which was purified by silica chromatography to give the free base. This was dissolved in ethyl acetate (10 mL) and treated with ethereal hydrogen chloride (2 mL, 1M). The solid formed was removed by filtration, washed with diethyl ether and dried to give the title compound as a solid (33 mg, 0.06 mmol).

$\delta_H$ (360 MHz, CD$_3$OD): 7.67–7.48 (5H, m), 7.35–7.29 (2H, m), 4.47 (1H, s), 4.13–4.06 (1H, m), 3.83–3.70 (3H, m), 2.95 (1H, dd, J 8.0 and 12.8 Hz), 2.71–2.67 (1H, m), 2.40–2.31 (4H, m), 1.91–1.87 (1H, m), 1.33 (3H, s), 1.14 (3H, s), 0.82–0.59 (4H, m). MS (ES$^+$) 491 (M+H).

EXAMPLE 16

(1R*,2R*,5S*,6S*)-2-(2-Cyclopropoxy-5-(trifluoromethoxy)-benzylamino)-6-(1H-tetrazol-5-yl)-1-phenyl-8-azabicyclo[3.2.1]octane Dihydrochloride Prepared according to the method of Example 5 from the product of Description 32 and 2-cyclopropoxy-5-(trifluoromethoxy)benzaldehyde.

$\delta_H$ (360 MHz, CD$_3$OD): 7.57–7.49 (5H, m), 7.37–7.30 (2H, m), 7.21 (1H, br s), 4.54 (1H, br s), 4.11–4.08 (2H, m), 3.77–3.70 (3H, m), 3.49 (1H, dd, J 9.7 and 14.6 Hz), 2.71 (1H, dd, J 5.4 and 14.7 Hz), 2.58–2.36 (3H, m), 2.10–2.00 (1H, m), 0.83–0.60 (4H, m). MS (ES$^+$) 501 (M+H).

EXAMPLE 17

(1R*,2R*,5S*,6R*)-2-(2-Cyclopropoxy-5-(trifluoromethoxy)-benzylamino)-1-phenyl-6-(1-methyl-1H-tetrazol-5-yl)-8-azabicyclo[3.2.1]octane Dihydrochloride Prepared according to the method of Example 5 from the product of Description 34 and 2-cyclopropoxy-5-(trifluoromethoxy)-benzaldehyde.

$\delta_H$ (400 MHz, CD$_3$OD): 7.52–7.47 (5H, m), 7.37–7.31 (2H, m), 7.21 (1H, d, J 2.3 Hz), 4.39–4.33 (1H, m), 4.14–4.10 (1H, m), 4.09 (3H, s), 3.76–3.71 (3H, m), 3.42 (1H, dd), 2.52–2.48 (3H, m), 2.38–2.34 (1H, m), 2.07–2.00 (1H, m), 0.84–0.61 (5H, m). MS (ES$^+$) 515 (M+H).

EXAMPLE 18

(1R*,2R*,5S*,6R*)-2-(2-Cyclopropoxy-5-(trifluoromethoxy)-benzylamino)-1-phenyl-6-(2-methyl-2H-tetrazol-5-yl)-8-azabicyclo[3.2.1]octane Dihydrochloride Prepared according to the method of Example 5 from the product of Description 35 and 2-cyclopropoxy-5-(trifluoromethoxy)-benzaldehyde.

$\delta_H$ (360 MHz, CD$_3$OD): 7.56–7.51 (5H, m), 7.35–7.29 (2H, m), 7.21 (1H, br s), 4.29 (3H, s), 4.11–4.04 (2H, m), 3.78–3.68 (3H, m), 3,48 (1H, dd, J 9.6 and 14.6 Hz), 2.80 (1H, dd, J 4.8 and 14.6 Hz), 2.76–2.38 (3H, m), 2.14–2.10 (1H, m), 0.82–0.59 (4H, m). MS (ES$^+$) 515 (M+H).

EXAMPLE 19

(1R*,2R*,3S*,5S*,6R*)-2-(2-Cyclopropoxy-5-(trifluoromethoxy)-benzylamnino)-3-fluoro-1-phenyl-6-(hydroxymethyl)-8-azabicyclo[3.2.1] octane Dihydrochloride Prepared according to the method of Example 5 from the product of Description 39 and 2-cyclopropoxy-5-(trifluoromethoxy)-benzaldehyde.

δ$_H$ (360 MHz, CD$_3$OD): 7.56–7.51 (3H, m), 7.45–7.42 (2H, m), 7.26 (1H, d, J 9.2 Hz), 7.17 (1H, dd, J 2.1 and 9.2 Hz), 6.66 (1H, d, J 2.1 Hz), 4.14 (1H, d, J 3.4 Hz), 3.77–3.71 (1H, m), 3.70–3.68 (1H, m), 3.59 (1H, dd, J 5.0 and 10 10.5 Hz), 3.45 (1H, dd, J 6.8 and 10.5 Hz), 3.09 (2H, s), 2.99 (1H, dd, J 9.2 and 14.5 Hz), 2.58–2.50 (1H, m), 2.40–2.29 (2H, m), 1.86 (1H, dd, J 4.7 and 14.7 Hz), 0.85–0.62 (4H, m). MS (ES$^+$) 481 (M+H).

EXAMPLE 20

(1R*,2R*,5S*,6R*)-6-(Bromomethyl)-2-(2-cyclopropoxy-5-(trifluoromethoxy)benzylamino)-1-phenyl-8-azabicyclo[3.2.1]octane (1R*,2R*,5S*,6R*)2-(2-Cyclopropoxy-5-(trifluoromethoxy)benzylamino)-6-20 (hydroxymethyl)-1-phenyl-8-azabicyclo[3.2.1]octane (Example 19; 225 mg, 0.49 mmol) was dissolved in dichloromethane (5 mL) and treated with triphenylphosphine (392 mg, 1.6 mmol) followed by carbon tetrabromide (497 mg, 1.5 mmol). The solution was then stirred at room temperature for 16 hours, before being poured into water (20 mL), extracted with dichloromethane (2×20 mL) and the extracts dried (MgSO$_4$). After concentration to approximately ¼ volume, the concentrated solution was applied to an acidic SCX ion exchange cartridge which was washed thoroughly with dichloromethane and ethyl acetate. The cartridge was then eluted with methanolic ammonia (200 mL, 2M) and the eluant concentrated in vacuo to give the title compound as a gum (208 mg, 0.4 mmol).

δ$_H$ (400 MHz, CDCl$_3$): 7.29–7.18 (5H, m), 7.05–6.99 (2H, m), 6.79 (1H, d, J 2.3 Hz), 3.73–3.59 (1H, m), 3.53 (1H, d, J 14.1 Hz), 3.49–3.45 (1H, m), 3.44–3.39 (1H, m), 3.36 (1H, d, J 14.5 Hz), 3.31 (1H, dd, J 6.7 and 9.8 Hz), 2.64–2.62 (1H, m), 2.44–2.37 (2H, m), 1.92–1.69 (4H, m), 1.38–1.33 (1H, m), 0.68–0.43 (4H, m). MS (ES$^+$) 525 and 527 (M+H).

EXAMPLE 21

(1R*,2R*,5S*,6R*)-2-(2-Cyclopropoxy-5-(trifluoromethoxy)-benzylamino)-6-[(methylsulphonyl)methyl]-1-phenyl-8-azabicyclo [3.2.1]octane Dihydrochloride (1R*,2R*,5S*,6R*)-6-(Bromomethyl)-2-(2-cyclopropoxy-5-(trifluoromethoxy)benzylamino)-1-phenyl-8-azabicyclo[13.2.1]octane (Example 20; 200 mg, 0.38 mmol) was dissolved in N,N-dimethylformamide (5 mL) and the solution treated with the sodium salt of methane-sulfinic acid (388 mg, 3.8 mmol). The resulting suspension was heated at 110° C. for 1 hour, then cooled and poured into water (50 mL). The mixture was extracted with ethyl acetate (2×20 mL), the extracts were dried (MgSO$_4$) and then concentrated to give a gum. This was purified by silica chromatography to give the pure free base, which was dissolved in ethyl acetate (10 mL). Ethereal hydrogen chloride (2 mL, 1M) solution was added and the solid formed was removed by filtration and recrystallized from methanol/diethyl ether to give the title compound as a white powder (120 mg, 0.20 mmol).

δ$_H$ (400 MHz, CD$_3$OD): 7.56–7.47 (5H, m), 7.33–7.27 (2H, m), 7.18 (1H, br s), 4.36 (1H, br s), 4.03 (1H, d, J 13.7 Hz), 3.72–3.64 (3H, m), 3.45 (1H, dd, J 8.8 and 14.6 Hz), 3.35–3.25 (2H, m), 3.10–3.04 (1H, m), 2.61–2.25 (3H, m), 2.05 (1H, dd, J 5.3 and 14.6 Hz), 1.97–1.93 (1H, m), 0.81–0.56 (4H, m). MS (ES$^+$) 525 (M+H).

What is claimed is:
1. A compound of the formula (I):

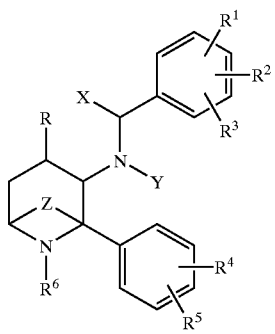

wherein
X represents hydrogen or a $C_{1-4}$alkyl group optionally substituted by a hydroxy group;
Y represents hydrogen, $C_{1-6}$alkyl or $C_{3-7}$cycloalkyl;
Z is —CR$^9$R$^{10}$CH$_2$— or —CH$_2$CR$^9$R$^{10}$—;
R represents hydrogen, fluorine, hydroxy, $C_{1-6}$alkyl or $C_{1-6}$alkoxy;
R$^1$ represents hydrogen, hydroxy, $C_{1-6}$alkyl, $C_{2-6}$alkenyl, $C_{3-7}$cycloalkyl, $C_{3-7}$cycloalkylC$_{1-4}$alkyl, $C_{1-6}$alkoxy, fluoroC$_{1-6}$alkoxy, hydroxyC$_{1-6}$alkyl, $C_{1-6}$alkoxyC$_{1-4}$alkyl, $C_{1-6}$alkoxyC$_{1-4}$alkoxy, fluoroC$_{1-6}$alkoxyC$_{1-4}$alkyl, $C_{2-6}$alkenyloxy, $C_{3-7}$cycloalkoxy, $C_{3-7}$cycloalkylC$_{1-4}$alkoxy, phenoxy, benzyloxy, cyano, halogen, NR$^a$R$^b$, SR$^a$, SOR$^a$, SO$_2$R$^a$, OSO$_2$R$^a$, NR$^a$COR$^{12}$, COR$^a$, CO$_2$R$^a$ or CONR$^a$R$^b$ where R$^a$ and R$^b$ each independently represent hydrogen, $C_{1-4}$alkyl or fluoroC$_{1-4}$alkyl;
R$^2$ represents hydrogen, halogen, $C_{1-6}$alkyl or $C_{1-6}$alkoxy;
or when R$^2$ is adjacent to R$^1$, they may be joined together such that there is formed a 5- or 6-membered saturated or unsaturated ring containing one or two atoms selected from nitrogen, oxygen, sulphur, NH or NR$^c$, which ring is optionally substituted by one, two or three groups selected from hydroxy, $C_{1-4}$alkyl, $C_{1-3}$alkoxyC$_{1-3}$alkyl, fluoroC$_{1-4}$alkyl, phenyl, =O or =S, where R$^c$ represents $C_{1-4}$alkyl, hydroxyC$_{1-4}$alkyl, $C_{1-4}$alkoxyC$_{1-4}$alkyl, fluoroC$_{1-4}$alkyl, phenyl or benzyl,
R$^3$ represents hydrogen, halogen, $C_{1-6}$alkyl, fluoroC$_{1-6}$alkyl, $C_{1-6}$alkoxy, fluoroC$_{1-6}$alkoxy, $C_{3-7}$cycloalkyl, $C_{3-7}$cycloalkylC$_{1-4}$alkyl, cyano, SR$^a$, SOR$^a$, SO$_2$R$^a$, NR$^a$R$^b$, NR$^a$COR$^{12}$, COR$^a$, CO$_2$R$^a$, CONR$^a$R$^b$ or $C_{1-4}$alkyl substituted by cyano, CO$_2$R$^a$ or CONR$^a$R$^b$ where R$^a$ and R$^b$ are as previously defined;
or R$^3$ represents a 5- or 6-membered aromatic heterocyclic group containing 1, 2, 3 or 4 heteroatoms, selected from nitrogen, oxygen and sulphur, which group is optionally substituted by one or two groups selected from $C_{1-6}$alkyl, $C_{1-6}$alkoxy, $C_{3-7}$cycloalkyl, $C_{3-7}$cycloalkylC$_{1-4}$alkyl, trifluoromethyl, OCF$_3$, NO$_2$, CN, SR$^a$, SOR$^a$, SO$_2$R$^a$, COR$^a$, CO$_2$R$^a$, phenyl, (CH$_2$)$_r$NR$^a$R$^b$, (CH$_2$)$_r$NR$^a$COR$_b$, (CH$_2$)$_r$CONR$^a$R$^b$, or CH$_2$C(O)R$^a$, where R$^a$ and R$^b$ are as previously defined and r is zero, 1 or 2;
R$^4$ represents hydrogen, halogen, $C_{1-6}$alkyl, $C_{1-6}$alkoxy, CF$_3$, OCF$_3$, NO$_2$, CN, SR$^a$, SOR$^a$, SO$_2$R$^a$, CO$_2$R$^a$, CONR$^a$R$^b$, $C_{2-6}$alkenyl, $C_{2-6}$alkynyl or $C_{1-4}$alkyl substituted by $C_{1-4}$alkoxy, where R$^a$ and R$^b$ are as previously defined;

R5 represents hydrogen, halogen, $C_{1-6}$alkyl, $CF_3$ or $C_{1-6}$alkoxy substituted by $C_{1-4}$alkoxy;

$R^6$ represents hydrogen, hydroxy, $COR^a$, $CO_2R^a$, $COCONR^aR^b$, $COCO_2R^a$, $C_{1-6}$alkyl optionally substituted by a group selected from ($CO_2R^a$, $CONR^aR^b$, hydroxy, CN, $COR^a$, $NR^aR^b$, $C(NOH)NR^aR^b$, CONHphenyl($C_{1-4}$alkyl), $COCO_2R^a$, $CONHNR^aR^b$, $C(S)NR^aR^b$, $CONR^aC_{1-6}$alkyl$R^{14}$, $CONR^{11}C_{2-6}$alkenyl, $CONR^{11}C_{2-6}$alkynyl, $COCONR^aR^b$, $CONR^aC(NR^b)NR^aR^b$, $CONR^a$heteroaryl, and phenyl optionally substituted by one, two or three substituents selected from $C_{1-6}$alkyl, $C_{1-6}$alkoxy, halogen and trifluoromethyl);

or $R^6$ represents a group of the formula —$CH_2C\equiv CCH_2NR^7R^8$ where $R^7$ and $R^8$ are as defined below;

or $R^6$ represents $C_{1-6}$alkyl, optionally substituted by oxo, substituted by a 5-membered or 6-membered heterocyclic ring containing 1, 2 or 3 nitrogen atoms optionally substituted by =O or =S and optionally substituted by a group of the formula —W—$NR^7R^8$ where W is $C_{1-6}$alkylene or $C_{3-6}$cycloalkyl;

$R^7$ represents hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy or hydroxyl;

$R^8$ represents hydrogen or $C_{1-4}$alkyl, $C_{1-4}$alkoxy, $C_{3-7}$cycloalkyl, $C_{3-7}$cycloalkyl$C_{1-4}$alkyl, or $C_{2-4}$alkyl substituted by a group selected from $C_{1-4}$alkoxy, hydroxyl, $CO_2R^a$, $NR^aR^b$, aryl, aryloxy, heteroaryl or a 4, 5 or 6 membered heteroaliphatic ring containing one or two heteroatoms selected from N, O and S;

or $R^7$, $R^8$ and the nitrogen atom to which they are attached form a heteroaliphatic ring of 4 to 7 ring atoms, optionally substituted by one or two groups selected from hydroxy, phenyl, benzyl or $C_{1-4}$alkoxy optionally substituted by a $C_{1-4}$alkoxy or hydroxyl group, and optionally containing a double bond, which ring may optionally contain an oxygen or sulphur ring atom, a group S(O) or S(O)$_2$ or a second nitrogen atom which will be part of a NH or $N^{RC}$ moiety where $R^c$ is as previously defined;

or $R^7$, $R^8$ and the nitrogen atom to which they are attached form a non-aromatic azabicyclic ring system of 6 to 12 ring atoms;

or W, $R^7$ and the nitrogen atom to which they are attached form a heteroaliphatic ring to 4 to 7 ring atoms which may optionally contain an oxygen ring atom;

$R^9$ represents hydrogen, hydroxy, oxo, $C_{1-6}$alkyl, $C_{2-6}$alkenyl, C2-6alkynyl, $C_{3-7}$cycloalkyl, $C_{3-7}$cycloalkyl$C_{1-4}$alkyl, fluoro$C_{1-6}$alkyl, $C_{1-6}$alkoxy, fluoro$C_{1-6}$alkoxy, hydroxy$C_{1-6}$alkyl, $C_{1-6}$alkoxy$C_{1-4}$alkyl, $C_{1-6}$alkoxy$C_{1-4}$alkoxy, fluoro$C_{1-6}$alkoxy$C_{1-4}$alkyl, $C_{2-6}$alkenyloxy, $C_{2-6}$alkynyloxy, $C_{3-7}$cycloalkoxy, $C_{3-7}$cycloalkyl$C_{1-4}$alkoxy, aryl, aryl($CH_2$), aryloxy, aryl($CH_2$)oxy, cyano, halogen, $NR^7R^8$, $CH_2NR^7R^8$, $SR^{12}$, $SOR^{12}$, $SO_2R^{12}$, $OSO_2R^{12}$, $NR^aCOR^{12}$, $CH(OH)R^{12}$, $COR^{12}$, $CO_2R^{12}$, $CONR^7R^8$, $CH_2OR^{13}$, heteroaryl or heteroaryl$C_{1-4}$alkyl, wherein $R^a$ is as previously defined;

$R^{10}$ represents hydrogen, halogen or hydroxy;

$R^{11}$ represents hydrogen or $C_{1-6}$alkyl;

$R^{12}$ represents hydrogen, $C_{1-6}$alkyl, $C_{1-6}$alkoxy, fluoro$C_{1-6}$alkyl or phenyl optionally substituted by one, two or three substituents selected from $C_{1-6}$alkyl, $C_{1-6}$alkoxy, halogen or trifluoromethyl;

$R^{13}$ represents $C_{1-4}$alkyl substituted by a group selected from hydroxy, $COR^a$, $CO_2R^a$, $CONR^aR^b$ and heteroaryl, where $R^a$ is as previously defined;

$R^{14}$ represents $OR^a$, $CONR^aR^b$ or heteroaryl;

or a pharmaceutically acceptable salt or N-oxide thereof; provided that when R, $R^4$, $R^5$, $R^6$, X and Y are hydrogen, and Z is —$CR^9R^{10}CH_2$— or —$CH_2CR^9R^{10}$— wherein $R^9$ and $R^{10}$ are hydrogen, then at least one of $R^1$, $R^2$, and $R^3$ is not hydrogen; and provided that when R, $R^4$, $R^5$, X and Y are hydrogen, Z is —$CR^9R^{10}CH_2$— or —$CH_2CR^9R^{10}$— wherein $R^9$ and $R^{10}$ are hydrogen, and $R^6$ is —$CO_2tBu$, then at least one of $R^1$, $R^2$, and $R^3$ is not hydrogen; and provided that when $R^1$ is 2-methoxy, and R, $R^2$, $R^4$, $R^5$, $R^6$, X and Y are hydrogen, and Z is —$CR^9R^{10}CH_2$— or —$CH_2CR^9R^{10}$— wherein $R^9$ and $R^{10}$ are hydrogen, then $R^3$ is not 5-trifluoromethoxy.

2. A compound as claimed in claim 1 wherein R is hydrogen or fluorine.

3. A compound as claimed in claim 1 wherein $R^1$ is a $C_{1-6}$alkoxy, fluoro$C_{1-6}$alkoxy or $C_{3-7}$cycloalkoxy group, or $R^1$ together with the group $R^2$ forms a 5-membered saturated ring containing one oxygen atom, which ring is optionally substituted by a methyl group.

4. A compound as claimed in claim 1 wherein $R^2$ is a hydrogen, fluorine or chlorine atom.

5. A compound as claimed in claim 1 wherein $R^3$ is a hydrogen or halogen atom or a fluoro$C_{1-6}$alkoxy group or a 5-membered aromatic heterocyclic group as defined in claim 1.

6. A compound as claimed in claim 1 wherein $R^4$ is hydrogen or fluorine.

7. A compound as claimed in claim 1 wherein $R^5$ is hydrogen.

8. A compound as claimed in claim 1 wherein $R^6$ is hydrogen or $C_{1-6}$alkyl, or a $C_{1-6}$alkyl group substituted by a 5-membered heterocyclic ring containing 2 or 3 nitrogen atoms as defined in claim 1.

9. A compound as claimed in claim 1 wherein Z is —$CR^9R^{10}CH_2$—.

10. A compound as claimed in claim 1 wherein $R^9$ is hydrogen, hydroxy, oxo, $C_{1-6}$alkoxy, $C_{1-6}$alkoxy$C_{1-4}$alkyl, hydroxy$C_{1-4}$alkyl, cyano, $NR^7R^8$, $CH_2NR^7R^8$, $SO_2R^d$, $CH(OH)R^{12}$, $COR^{12}$, $CO_2R^{12}$, $CONR^7R^8$, phenyl, heteroaryl, heteroaryl$C_{1-4}$alkyl or $CH_2OR^{13}$, where said phenyl is optionally substituted by one or two substituents selected from $C_{1-4}$alkyl, $C_{1-4}$alkoxy, halogen or trifluoromethyl.

11. A compound as claimed in claim 1 wherein $R^{10}$ is hydrogen, fluorine or hydroxy.

12. A compound as claimed in claim 1 wherein X is hydrogen, methyl or hydroxymethyl.

13. A compound as claimed in claim 1 wherein Y is hydrogen or $C_{1-4}$alkyl.

14. A compound of the formula (Ia):

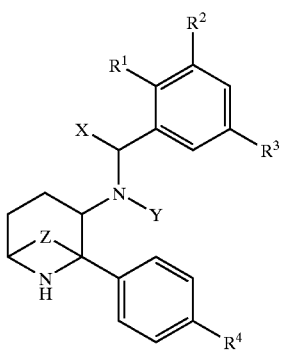

(Ia)

wherein $R^1$, $R^2$, $R^3$, $R^4$, X and Y are as defined in claim 1 and Z is —$CR^9R^{10}CH_2$—;
or a pharmaceutically acceptable salt thereof.

15. A compound as claimed in claim 1 selected from the group consisting of:

1R*,2R*,5S*)-2-(3,5-bis(trifluoromethyl)benzylamino)-1-phenyl-8-azabicyclo[3.2.1]octane;

(1R*,2R*,5S*)-2-(2-cyclopropyloxy-5-[5-(trifluoromethyl)tetrazol-1-yl]benzylamino)-1-phenyl-8-azabicyclo[3.2.1]octane;

(1R*,2R*,5S*)-2-(2-methoxy-5-(trifluoromethoxy)benzylamino)-8-benzyl-1-phenyl-8-azabicyclo[3.2.1]octane;

(1R*,2R*,5S*)-2-(2-Cyclopropoxy-5-(trifluoromethoxy)-benzylamino)-1-phenyl-8-azabicyclo[3.2.1]octane;

(1R*,2R*,5S*,6R*)-2-(2-methoxy-5-(trifluoromethoxy)benzylamino)-1-phenyl-6-phenylsulphonyl-8-azabicyclo[3.2.1]octane;

(1R*,2R*,5S*,9S*)- and (1R*,2R*,5S*,9R*)-2-[1-(2-methoxy-5-(trifluoromethoxy)phenyl)ethylamino]-1-phenyl-8-azabicyclo[3.2.1]octane;

(1R*,2R*,5S*,6R*)-2-(2-cyclopropoxy-5-(trifluoromethoxy)-benzylamino)-6-(hydroxymethyl)-1-phenyl-8-azabicyclo[3.2.1]octane;

(1R*,2R*,5S*)-2-(2-chloro-5-(trifluoromethoxy)benzylamino)-1-phenyl-8-azabicyclo[3.2.1]octane;

(1R*,2R*,5S*,6R*)-2-(2-cyclopropoxy-5-(trifluoromethoxy)-benzylamino)-6-[1-(3-hydroxy)propyloxymethyl]-1-phenyl-8-azabicyclo[3.2.1]octane;

(1R*,2R*,5S*,6R*)-2-(2-cyclopropoxy-5-(trifluoromethoxy)-benzylamino)-6-(tert-butoxycarbonyl)-1-phenyl-8-azabicyclo[3.2.1]octane;

(1R*,2R*,5S*,6R*)-2-(2-cyclopropoxy-5-(trifluoromethoxy)-benzylamino)-6-(N-methoxy-N-methylcarboxamido)-1-phenyl-8-azabicyclo[3.2.1]octane;

(1R*,2R*,5S*,6R*)-2-(2-cyclopropoxy-5-(trifluoromethoxy)-benzylamino)-6-acetyl-1-phenyl-8-azabicyclo[3.2.1]octane;

(1R*,2R*,5S*,6R*,R*) and (1R*,2R*,5S*,6R*,S*)-2-(2-cyclopropoxy-5-(trifluoromethoxy)benzylamino)-6-(1-hydroxy)ethyl-1-phenyl-8-azabicyclo[3.2.1]octane;

(1R*,2R*,5S*,6R*)-2-(2-cyclopropoxy-5-(trifluoromethoxy)-benzylamino)-6-(1-hydroxy-1-methyl)ethyl-1-phenyl-8-azabicyclo[3.2.1]octane;

(1R*,2R*,5S*,6S*)-2-(2-cyclopropoxy-5-(trifluoromethoxy)-benzylamino)-6-(1H-tetrazol-5-yl)-1-phenyl-8-azabicyclo[3.2.1]octane;

(1R*,2R*,5S*,6S*)-2-(2-cyclopropoxy-5-(trifluoromethoxy)-benzylamino)-1-phenyl-6-(1-methyl-1H-tetrazol-5-yl)-8-azabicyclo[3.2.1]octane;

(1R*,2R*,5S*,6S*)-2-(2-cyclopropoxy-5-(trifluoromethoxy)-benzylamino)-1-phenyl-6-(2-methyl-2H-tetrazol-5-yl)-8-azabicyclo[3.2.1]octane;

(1R*,2R*,3S*,5S*,6R*)-2-(2-cyclopropoxy-5-(trifluoromethoxy)-benzylamino)-3-fluoro-1-phenyl-6-(hydroxymethyl)-8-azabicyclo[3.2.1]octane;

(1R*,2R*,5S*,6R*)-6-(bromomethyl)-2-(2-cyclopropoxy-5) (trifluoromethoxy)benzylamino)-1-phenyl-8-azabicyclo[3.2.1]octane; and (1R*,2R*,5S*,6R*)-2-(2-cyclopropoxy-5-(trifluoromethoxy)-benzylamino)-6-[(methylsulphonyl)methyl]-1-phenyl-8-azabicyclo[3.2.1]octane;

or a pharmaceutically acceptable salt thereof.

16. A compound as claimed in claim 1 wherein the stereochemistry of the 1- 2-, and 5-positions is as shown in formula (Ib):

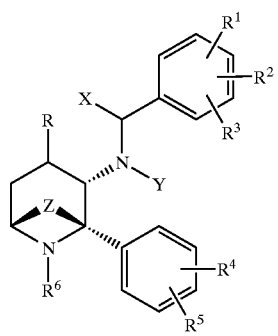

(Ib)

17. A pharmaceutical composition comprising a compound as claimed in claim 1, together with at least one pharmaceutically acceptable carrier or excipient.

18. A method for the treatment of physiological disorders associated with an excess of tachykinins, which method comprises administration to a patient in need thereof of a tachykinin reducing amount of a compound of the formula (I):

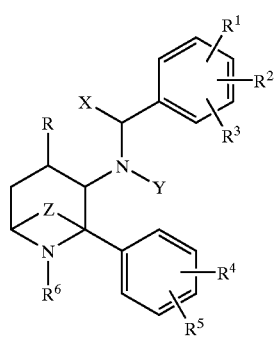

(I)

wherein

X represents hydrogen or a $C_{1-4}$alkyl group optionally substituted by a hydroxy group;

Y represents hydrogen, $C_{1-6}$alkyl or $C_{3-7}$cycloalkyl;

Z is —$CR^9R^{10}CH_2$— or —$CH_2CR^9R^{10}$—;

R represents hydrogen, fluorine, hydroxy, $C_{1-6}$alkyl or $C_{1-6}$alkoxy;

$R^1$ represents hydrogen, hydroxy, $C_{1-6}$alkyl, $C_{2-6}$alkenyl, $C_{3-7}$cycloalkyl, $C_{3-7}$cycloalkyl$C_{1-4}$alkyl, $C_{1-6}$alkoxy, fluoro$C_{1-6}$alkoxy, hydroxy$C_{1-6}$alkyl, $C_{1-6}$alkoxy$C_{1-4}$alkyl, $C_{1-6}$alkoxy$C_{1-4}$alkoxy, fluoro$C_{1-6}$alkoxy$C_{1-4}$alkyl, $C_{2-6}$alkenyloxy, $C_{3-7}$cycloalkoxy, $C_{3-7}$cycloalkyl$C_{1-4}$alkoxy, phenoxy, benzyloxy, cyano, halogen, $NR^aR^b$, $SR^a$, $SOR^a$, $SO_2R^a$, $OSO_2R^a$, $NR^aCOR^{12}$, $COR^a$, $CO_2R^a$ or $CONR^aR^b$ where $R^a$ and $R^b$ each independently represent hydrogen, $C_{1-4}$alkyl or fluoro$C_{1-4}$alkyl;

$R^2$ represents hydrogen, halogen, $C_{1-6}$alkyl or $C_{1-6}$alkoxy;

or when $R^2$ is adjacent to $R^1$, they may be joined together such that there is formed a 5- or 6-membered saturated or unsaturated ring containing one or two atoms selected from nitrogen, oxygen, sulphur, NH or NRC, which ring is optionally substituted by one, two or three groups selected from hydroxy, $C_{1-4}$alkyl, $C_{1-3}$alkoxy$C_{1-3}$alkyl, fluoro$C_{1-4}$alkyl, phenyl, =O or =S, where $R^c$ represents $C_{1-4}$alkyl, hydroxy$C_{1-4}$alkyl, $C_{1-4}$alkoxy$C_{1-4}$alkyl, fluoro$C_{1-4}$alkyl, phenyl or benzyl, $R^3$ represents hydrogen, halogen, $C_{1-6}$alkyl, fluoro$C_{1-6}$alkyl, $C_{1-6}$alkoxy, fluoro$C_{1-6}$alkoxy, $C_{3-7}$cycloalkyl, $C_{3-7}$cycloalkyl$C_{1-4}$alkyl, cyano, $SR^a$, $SOR^a$, $SO_2R^a$, $NR^aR^b$, $NR^aCOR^{12}$, $COR^a$, $CO_2R^a$, $CONR^aR^b$ or $C_{1-4}$alkyl substituted by cyano, $CO_2R^a$ or $CONR^aR^b$ where $R^a$ and $R^b$ are as previously defined;

or $R^3$ represents a 5- or 6-membered aromatic heterocyclic group containing 1, 2, 3 or 4 heteroatoms, selected from nitrogen, oxygen and sulphur, which group is optionally substituted by one or two groups selected from $C_{1-6}$alkyl, $C_{1-6}$alkoxy, $C_{3-7}$cycloalkyl, $C_{3-7}$cycloalkyl$C_{1-4}$alkyl, trifluoromethyl, $OCF_3$, $NO_2$, CN, $SR^a$, $SOR^a$, $SO_2R^a$, $COR^a$, $CO_2R^a$, phenyl, —$(CH_2)_rNR^aR^b$, $(CH_2)_rNR^aCOR^b$, —$(CH_2)_rCONR^aR^b$, or $CH_2C(O)R^a$, where $R^a$ and $R^b$ are as previously defined and r is zero, 1 or 2;

$R^4$ represents hydrogen, halogen, $C_{1-6}$alkyl, $C_{1-6}$alkoxy, $CF_3$, $OCF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, where $R^a$ and $R^b$ are as previously defined;

$R^5$ represents hydrogen, halogen, $C_{1-6}$alkyl, $CF_3$ or $C_{1-6}$alkoxy substituted by $C_{1-4}$alkoxy;

$R^6$ represents hydrogen, hydroxy, $COR^a$, $CO_2R^a$, $COCONR^aR^b$, $COCO_2R^a$, $C_{1-6}$alkyl optionally substituted by a group selected from ($CO_2R^a$, $CONR^aR^b$, hydroxy, CN, $COR^a$, $NR^aR^b$, $C(NOH)NR^aR^b$, CONHphenyl($C_{1-4}$alkyl), $COCO_2R^a$, $CONHNR^aR^b$, $C(S)NR^aR^b$, $CONR^aC_{1-6}$alkyl$R^{14}$, $CONR^{11}C_{2-6}$alkenyl, $CONR^{11}C_{2-6}$alkynyl, $COCONR^aR^b$, $CONR^aC(NR^b)NR^aR^b$, $CONR^a$heteroaryl, and phenyl optionally substituted by one, two or three substituents selected from $C_{1-6}$alkyl, $C_{1-6}$alkoxy, halogen and trifluoromethyl);

or $R^6$ represents a group of the formula —$CH_2C\equiv CCH_2NR^7R^8$ where $R^7$ and $R^8$ are as defined below;

or $R^6$ represents $C_{1-6}$alkyl, optionally substituted by oxo, substituted by a 5-membered or 6-membered heterocyclic ring containing 1, 2 or 3 nitrogen atoms optionally substituted by =O or =S and optionally substituted by a group of the formula —W—$NR^7R^8$ where W is $C_{1-6}$alkylene or $C_{3-6}$cycloalkyl;

$R^7$ represents hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy or hydroxyl;

$R^7$ $R^8$ represents hydrogen or $C_{1-4}$alkyl, $C_{1-4}$alkoxy, $C_{3-7}$cycloalkyl, $C_{3-7}$cycloalkyl$C_{1-4}$alkyl, or $C_{2-4}$alkyl substituted by a group selected from $C_{1-4}$alkoxy, hydroxyl, $CO_2R^a$, $NR^aR^b$, aryl, aryloxy, heteroaryl or a 4, 5 or 6 membered heteroaliphatic ring containing one or two heteroatoms selected from N, O and S;

or $R^7$, $R^8$ and the nitrogen atom to which they are attached form a heteroaliphatic ring of 4 to 7 ring atoms, optionally substituted by one or two groups selected from hydroxy, phenyl, benzyl or $C_{1-4}$alkoxy optionally substituted by a $C_{1-4}$alkoxy or hydroxyl group, and optionally containing a double bond, which ring may optionally contain an oxygen or sulphur ring atom, a group S(O) or $S(O)_2$ or a second nitrogen atom which will be part of a NH or NRC moiety where $R^c$ is as previously defined;

or $R^7$, $R^8$ and the nitrogen atom to which they are attached form a non-aromatic azabicyclic ring system of 6 to 12 ring atoms;

or W, $R^7$ and the nitrogen atom to which they are attached form a heteroaliphatic ring to 4 to 7 ring atoms which may optionally contain an oxygen ring atom;

$R^9$ represents hydrogen, hydroxy, oxo, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, fluoro$C_{1-6}$alkyl, $C_{1-6}$alkoxy, fluoro$C_{1-6}$alkoxy, hydroxy$C_{1-6}$alkyl, $C_{1-6}$alkoxy$C_{1-4}$alkyl, $C_{1-6}$alkoxy$C_{1-4}$alkoxy, fluoro$C_{1-6}$alkoxy$C_{1-4}$alkyl, $C_{2-6}$alkenyloxy, $C_{2-6}$alkynyloxy, $C_{3-7}$cycloalkoxy, $C_{3-7}$cycloalkyl$C_{1-4}$alkoxy, aryl, aryl($CH_2$), aryloxy, aryl($CH_2$)oxy, cyano, halogen, $NR^7R^8$, $CH_2NR^7R^8$, $SR^{12}$, $SOR^{12}$, $SO_2R^{12}$, $OSO_2R^{12}$, $NR^aCOR^{12}$, $CH(OH)R^{12}$, $COR^{12}$, $CO_2R^{12}$, $CONR^7R^8$, $CH_2OR^{13}$, heteroaryl or heteroaryl$C^{1-4}$alkyl, wherein $R^a$ is as previously defined;

$R^{10}$ represents hydrogen, halogen or hydroxy;

$R^{11}$ represents hydrogen or $C_{1-6}$alkyl;

$R^{12}$ represents hydrogen, $C_{1-6}$alkyl, $C_{1-6}$alkoxy, fluoro$C_{1-6}$alkyl or phenyl optionally substituted by one, two or three substituents selected from $C_{1-6}$alkyl, $C_{1-6}$alkoxy, halogen or trifluoromethyl;

$R^{13}$ represents $C_{1-4}$alkyl substituted by a group selected from hydroxy, $COR^a$, $CO_2R^a$, $CONR^aR^b$ and heteroaryl, where $R^a$ is as previously defined;

$R^{14}$ represents $OR^a$, $CONR^aR^b$ or heteroaryl;

or a pharmaceutically acceptable salt or N-oxide thereof.

19. A method according to claim 18 for the treatment of pain or inflammation, migraine, emesis, postherpetic neuralgia, depression or anxiety.

* * * * *